(12) United States Patent
Sharma et al.

(10) Patent No.: US 7,718,788 B2
(45) Date of Patent: May 18, 2010

(54) POLYNUCLEOTIDE FROM A NOVEL GENE FROM DROUGHT STRESS TOLERANT TEA PLANT

(75) Inventors: Priti Sharma, Palampur (IN); Sanjay Kumar, Palampur (IN); Paramvir Singh Ahuja, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/430,519

(22) Filed: May 8, 2006

(65) Prior Publication Data

US 2007/0083954 A1 Apr. 12, 2007

Related U.S. Application Data

(63) Continuation of application No. 10/109,363, filed on Mar. 27, 2002, now abandoned.

(51) Int. Cl.
*C12N 15/29* (2006.01)
(52) U.S. Cl. .................................................. 536/23.6
(58) Field of Classification Search .................. None
See application file for complete search history.

(56) References Cited

U.S. PATENT DOCUMENTS

| 5,656,474 A | 8/1997 | Tabaeizadeh et al. |
| 5,892,009 A | 4/1999 | Thomashow et al. |
| 5,981,729 A | 11/1999 | Chun et al. |
| 6,218,527 B1 | 4/2001 | Kim et al. |
| 6,245,905 B1 | 6/2001 | Kim et al. |

OTHER PUBLICATIONS

Sheen et al. Science, vol. 274, Dec. 13, 1996, pp. 1900-1902.*
Kaye et al. Plant Physiology, 1998, vol. 116, pp. 1367-1377.*
Whisstock J.C. et al. Prediction of protein function from protein sequence and structure. Q Rev Biophys. Aug. 2003;36(3):307-40. Review.*
Yamaguchi-Shinozaki, et al., "A Novel *cis*-Acting in an Arabidopsis Gene Is Involved in Responsiveness to Drought, Low-Temperature, or High-Salt Stress," the Plant Cell, 1994, vol. 6, pp. 251-264.
Li, et al., "Molecular cloning of a novel water channel from rice: its product expression in *Xenopus* oocytes and involvement in chilling tolerance," *Plant Science*, 154 (2000) pp. 43-51.

* cited by examiner

*Primary Examiner*—Cynthia Collins
(74) *Attorney, Agent, or Firm*—Reed Smith LLP; Nanda P. B. A. Kumar

(57) ABSTRACT

The present invention relates to a novel polynucleotide comprising SEQ ID NO. 1 useful for water-stress tolerance in biological systems, where the polynucleotide is differentially expressed in Tea plant under drought conditions.

4 Claims, 6 Drawing Sheets

POLYNUCLEOTIDE FROM A NOVEL GENE FROM DROUGHT STRESS TOLERANT TEA PLANT

This is a continuation of application Ser. No. 10/109,363, filed Mar. 27, 2002, now abandoned all of which is incorporated by reference.

BACKGROUND OF THE INVENTION

1. Field of the Invention

The present invention relates to three novel genes of SEQ ID Nos. 1-3 useful for water-stress tolerance in biological systems, wherein said genes are differentially expressed in Tea plant under drought conditions and a method of introducing said genes into a biological system to help develop water stress tolerance.

2. Prior Art

Crop performance is sensitive to a number of biotic and abiotic factors, wherein drought stress constitutes an important yield-limiting determinant. Drought stress in context to the present invention refers to the situation when the amount of water in the plant is not sufficient to meet the transpirational requirements of the plant that leads to altered visible symptoms such as leaf curling. Drought should also be quantifiable through an important physiological parameter, leaf water potential (a measure of water status within the leaf tissue). Plant response to water deficit is dependent on the amount of water lost, the rate of loss, the duration of drought stress, the plant variety/species under consideration, developmental stage of the plant, and other environmental variables such as temperature, relative humidity etc.

Stress affects many metabolic pathways and structures, which may be the result of some up or down-regulated genes. Many of the water deficit induced genes encode gene products predicted to protect cellular function. One often noticed response of the plant is the accumulation of metabolically compatible solutes such as proline, glycine betaine, pinitol, carnitine, mannitol, sorbitol, polyols, trehalose, sucrose, oligosachharides and fructans in large quantities. These are chemically dissimilar and are excluded from the surface of the proteins, thus keeping the proteins preferentially hydrated. Accumulation of these compounds results in decreased water potential thus, facilitating water movement in the cell and helps in maintaining the turgor, a mechanism proposed to safeguard against water deficit.

These compounds have capability to (a) stabilize the membranes and other macromolecules such as nucleic acids and proteins, and can function as scavenger of free radicals. Indeed the transgenic plants over-expressing the genes responsible for the synthesis of these compounds were found to be more tolerant as compared to the wild types under the situation of water deficiency. Classical studies include: (a) transgenic tobacco overexpressing SacB gene (encoding levan-sucrase) from *Bacillus subtilis* accumulated fructan several folds that showed significantly greater growth and dry weight accumulation in response to drought stress (Pilon-Smits, E. A. H., Ebskarnp, M. J. M., Paul, M. J., Jeuken, M. J. W., Weisbeek, P. J. and Smeekens, S. C. M. (1995) Improved performance of transgenic fructan-accumulating tobacco under drought stress. Plant Physiol. 107:125-130); (b) Transgenic tobacco overexpressing P5CS ($\Delta^1$-pyrroline-5-carboxylate synthetase; the enzyme involved in the proline biosynthesis from L-glutamate via $\Delta^1$-pyrroline-5-carboxylate) from mothbean (*Vigna aconitifolia*) lead to 10-18 fold increase in proline content and showed better growth under water stress compared to the wild type (Kavi, K. P. B., Hong, Z., Miao, G-H., Hu C. A. A. and Verma, D. P. S.(1995) Plant Physiol. 108:1387-1394); (c) Transgeric tobacco expressing TPS1 gene (synthesizing trehalose-6-phosphate synthase) from yeast accumulated trehalose and showed better drought tolerance compared to the wild types (Holmstorm, K. O., Mantyla, E., Mandal, W. A., Palva, E. T., Tunnela, O. E. and Londesborough J. (1996) Drought tolerence in tobacco. Nature. 379: 683-684); (d) Transgenic tobacco overexpressing betB gene (synthesizing betaine aldehyde dehydrogenase) from *E. coli* showed better performance under osmotic stress conditions (Holmstrom, K. O., Welin, B. and Mandal, A. (1994) Production of the *Escherichia coli* betaine-aldehyde dehydrogenase an enzyme required for the synthesis of the osmoprotectant glycine betaine, in transgenic plants. Plant J. 6:749-758); (e) Transgenic tobacco expressing imtl gene (synthesizing myo-inositol-o-methyl transferase and involved in D-ononitol biosynthesis) from *Mesembryanthemum crystallinum* showed more adaptation to water stress (Sheveleva, E., Chmara, W., Bohnert, H. J. and Jensen, R. G. (1997) Increased salt and drought tolerence by D-Ononitol production in transgenic *Nicotiana tabacum*. Plant Physiol.5: 1211-1219); (f) Production of some of these osmo-protectants under drought stress is mediated through the plant hormone abscisic acid (ABA).

Recently, 9-cis-epoxycarotenoid dioxygenase gene (NCED), involved in ABA synthesis has been found to be strongly induced under water deficit in the 8-day-old cowpea plants (Iuchi, S., Kobayashi., Yamaguchi-Shinozaki, K. and Shinozaki, K. (2000) A stress-inducible gene for 9-cis-epoxycarotenoid dioygenase involved in abscisic acid biosynthesis under water stress in drought-tolerant cowpea. Plant physiol. 123:553-562). NCED mRNA was found to be increased both In reply to: water stressed leaves and roots of tomato (Thompson, A. J., Jackson, A. C., Parker, R. A., Morpeth, D. R., Burbidge, A. and Taylor, I. B. (2000) Abscisic acid biosynthesis in tomato: regulation of dioxygenase mRNA by light/dark cycles, water stress and abscisic acid. Plant. Mol. Biol. 42:833-845).

Apart from the osmolytes assisting in maintaining the hydration status, drought or osmotically stressed plants, synthesize several genes, which produce water channel proteins and water transport proteins such as membrane proteins of family aquaporins that can alter the cellular water potential and thus, protect against water deficit (Chrispeels, M. J. and Agre, P. (1994) Water channel proteins of plants and animal cells. Trends in Biochem Sci. 19:421-425; Bohnert H, J. and Jensen, R. G. (1996).

Strategies for engineering water-stress tolerance in plants. TIBTECH. 14:89-97; Johansson, I., Larsson, C., Ek B. and Kjellbom, P. (1996) The major integral proteins of spinach leaf plasma membranes are putative aquaporins and are phosphorylated in response to Ca and apoplastic water potential. The Plant Cell. 8:1181-1191. Accumulation of LEAs to high concentrations also coincides with the acquisition of desiccation tolerance. One of the groups-3 of LEA proteins is predicted to play a role in the sequestration of ions that are concentrated during cellular dehydration. Another group-5 of LEA proteins are predicted to sequester ions during water loss. The maintenance of total water potential during water deficit can be achieved by osmotic adjustment. Two proteins, osmotin and nonspecific lipid transfer proteins, are stress induced and are thought to play a role in controlling pathogens. Nonspecific lipid transfer proteins are induced by drought (Plant A. L., Cohen, A., Moses, M. S. and Bray, E. A. (1991) Nucleotide sequence and spatial expression pattern of a drought abscisic acid induced gene in tomato. Plant Physiol. 97:900-906; Toress-Schumann, S., Godoy, J. A. and Pintor- Toro, J. A. (1992) A probable lipid transfer protein is induced by NaCl in stems of tomato plants. Plant Mol. Biol.18:749-757).

Heat shock proteins that are induced by water deficit (Borkird, C., Simoens, C., Villarroel, R. and VanMontagu M. (1991) Gene associated with water-stress adaptation of rice cells and identification of two genes as hsp 70 and ubiquitin. Physiol. Plant. 82: 449-457; Almoguera, C. and Jordano, J. (1992) Developmental and environmental concurrent expression in sunflower dry-seed-stored low-molecular-weight heat shock protein and Lea mRNAs. Plant Mol. Biol. 19:781-792) may be involved in refolding of proteins in order to regain their function, or the prevention of protein aggregation (Vierling E. (1991) the roles of heat shock proteins in plants. Annual review of Plant Physiol. and Plant Mol. Biol. 42:579-620) during drought.

Small HSPs are another type of proteins those have been associated with plant desiccation tolerance. Small HSPs might act as molecular chaperones during seed dehydration and first few days of rehydration (Hoekstra, F, A., Golovina, E, A. and Buitink, J. (2001) Mechanisms of plant desiccation tolerance. Trends in Plant Science. 6(9): 43-439). OsHSP110 accumulated in shoots of rice seedlings in response to salinity, drought and low temperature apart from heat shock. It has been shown that two of the hsps, hsp70 in maize and hsp27 in soybean can also be induced by water stress (Sachs, M. M. and David Ho, T. H. (1986). Alterations of gene expression during environmental stress in plants. Ann. Rev. Plant Physiol. 37: 363-376). Most of the changes in gene expression occur during dehydration and thus many dehydration-specific gene products have been isolated but very few rehydration-specific proteins are known (Bernacchia, G., Schwall, G., Lottspeich, F., Salamini, F., and Bartels, D. (1995) Molecular Characterization of the Rehydration process in the Resurrection Plant *Craterostigma Plantagineum*. EMBO J 14: 610-618).

Complex regulatory and signaling processes, most of which are not understood, control the expression of genes during water deficit. Genes involved in two types of protein degrading mechanisms, proteases and ubiquitin are induced by water deficit. The gene products may be involved in degradation of proteins that are denatured during cellular water loss. Also, thiol protease an enzyme involved in degradation of proteins that have been denatured by stress, is induced by water deficit (Guerrero, F. D., Jones, J. T. and Mullet, J. E. (1990) Turgor-responsive gene transcription and RNA levels increases rapidly when pea shoots are wilted: sequence and expression of three inducible genes. Plant Mol. Biol. 15: 11-26).

Neale, A. D., Blomstedt, C. K., Bronson, P., Le, T.-N., Guthridge, K., Evans, J., Gaff, D. F. and Hamill, J. D. (2000. The isolation of genes from the resurrection grass *Sporobulus stapfianus* which are induced during severe drought stress. Plant, Cell and Environment. 23:265-277) isolated drought stress induced genes from resurrection grass *Sporobolus stapfianus*. Detected genes were found to encode an eIF1 translation initiation factor, two drought stress-inducible glycine-rich proteins, a tonoplast-intrinsic protein (TIP) and an early light-inducible protein (ELIP). Previously, no such gene products have been found to be associated with drought stress. This is the first report suggesting that a gene encoding an eLF1 translation initiation factor may have a role in the drought stress response of plants.

Several different stresses may trigger the same or similar signal transduction pathways. The plant hormone ABA also accumulates in response to the physical phenomenon of loss of water caused by the different stresses, and elevation in endogenous ABA content is known to induce certain water-deficit induced genes. Therefore, ABA accumulation is a step in one of the signal transduction pathways that induces genes during water deficit. Various protein kinases have been reported in plants and are thought to function in phosphorylation processes in various signal transduction pathways, including water-stress and ABA responses.

A cDNA, pKABA1, corresponding to a protein kinase, which is induced by ABA, has been isolated (Anderberg, R. J. and Walker-Simmons, M. K. (1992) Isolation of wheat cDNA clone for an abscisic acid-inducible trascript with homology to protein kinases.

Proc. Natl. Acad. Sci. USA 89: 10183-10187). A new homoebox-containing gene, Athb-12 and Athb-7 are induced by water deficit and exogenous ABA treatment but time course experiment have shown that both of these are regulated in a different manner (Lee, Y. H. and Chun. J. Y. (1998) A new homeodomain-leucine zipper gene from *Arabidopsis thaliania* induced by water stress and abscisic acid treatment. Plant Mol. Biol. 37: 377-384).

Available evidences suggest that stress induced responses may be ABA mediated or independent of ABA (Shinozaki, K. and Yamaguchi-Shinozaki, K. (1997) Gene expression and signal transduction in water-stress response. Plant Physiol. 115: 327-334). ABA mediated gene response may require or may not require protein synthesis to take place. The induction of mRNA of rd22 gene by ABA, which showed homology to an unidentified seed protein of *Vicia faba*, required protein synthesis to take place since cycloheximide inhibited induction of the gene (Yamaguchi-Shinozaki K. and Shinozaki, K. (1993) The plant hormone abscisic acid mediates the drought-induced expression but not the seed-specific expression of rd22, a gene responsive to dehydration stress in *Arabidopsis thaliana*. Mol. Gen. Genet. 238:17-25).

Structure analysis of the gene revealed the presence of regulatory sequences (cis-acting motif) asl (TGACG; SEQ ID NO: 4) and sp1 (GGGCGG; SEQ ID NO: 5) at −463 and −443 positions, respectively (Briggs, M. R., Kadonaga, J. T., Bell, S. P. and Tijan, R. (1986). Purification and Biochemical characterization of the promoter-specific transcription factor, Spl. Science 234:47-52; Lam, E., Benfey, P. N., Gilmartin, P. M., Fang, R. X. and Chua N-H. (1989). Site specific mutations alter in vitro factor binding and change promoter expression pattern in transgenic plants. Proc. Natl. Acad. Sci. USA. 86: 7890-7894). Also, were present the sequences that resembled myb (a family of transcription factors with Tip cluster motif) recognition elements TGGTTAG (SEQ ID NO: 6) at −144 and −666 and 2 bHLH (basic helix-loop-helix; MYC) recognition elements (CACATG; SEQ ID NO: 7) at −200 and −191 position. A cDNA (rd22BP1) encoding a MYC related DNA binding protein was isolated, which was found to encode a 68 kD protein that has a typical DNA binding domain of a basic region helix-loop-helix leucine zipper motif in MYC-related transcription factors.

The protein indeed binds to the MYC recognition site (Abe, H., Yamaguchi-Shinozaki, K., Urao, T., Iwasaki, T., Hosokawa, D. and Shinozaki, K. (1997) Role of Arabidopsis MYC and MYB Homologs in Drought- and Abscisic Acid-Regulated Gene Expression. The Plant Cell. 9:1859-1868). A drought and ABA inducible gene has also been cloned that encodes MYB-related protein ATMYB2. Both rd22BP 1 (MYC) and ATMYB2 (MYB) proteins were shown to function as transcription activators in the dehydration and ABA-inducible expression of the rd22 gene (Abe, H., Yamaguchi-Shinozaki, K., Urao, T., Iwasaki, T., Hosokawa, D and Shinozaki, K. (1997). Role of Arabidopsis WC and MYB Homologs in Drought- and Abscisic Acid-Regulated Gene Expression. The Plant Cell. 9:1859-1868).

In contrast to rd22 in Arabidopsis, HVA22 gene in barley is induced in response to drought and ABA, but is also induced in the presence of cycloheximide. The promoter region of HVA22 contains ABA responsive complex ABRE3, CE1 and another ABA responsive complex that relies on the interaction of a G-box with another yet unidentified coupling element (Shen, Q. and Ho, T-H D. (1995) Functional Dissection of an Abscisic Acid (ABA)-Inducible gene Reveals Two Independent ABA-Responsive Complexes Each Containing a G-Box and a novel cis-Acting Element. The Plant Cell. 7:295-307)

Yamaguchi-Shinozaki K and Shinozaki, K. (1993. Characterization of the expression of dessication-responsive rd29 gene of *Arabidopsis thaliana* and analysis of its promoter in transgenic plants. Mol. Gen. Genet. 236: 331-340) cloned a dehydration responsive gene rd29A that was independent of ABA responsive pathway. The sequence TACCGACAT (SEQ ID NO: 8) was found to be regulating the genes induced under drought conditions and was found in the promoter regions of other dehydration inducible genes.

Upon over-expression of DREBIA (a dehydration responsive element binding protein) under the control of rd29a promoter in *A. thaliana*, a number of stress tolerant genes were expressed and resulted in an improved tolerance under drought and several other stresses (Kasuga, M., Liu, Q., Miura, S., Yamaguchi-Shinozaki, K. and Shinozaki, K. (1999) Improving plant drought, salt, and freezing tolerance by gene transfer of a single stress-inducible transcription factor. Nature Biotechnology. 17:287-291).

Analysis of another gene of DRE-binding protein DREB2 showed that its promoter was induced under water stress in transgenic arabidopsis (Nakasimha, K., Shinwari, Z. K., Sakuma, Y., Seki, M., Miura, S., Shinozaki, K. and Yamaguchi-Shinozaki, K.(2000) Organization and expression of two Alabidopsis DREB2 genes encoding DRE-binding proteins involved in dehydration and high salinity responsive gene expression. Plant. Mol. Biol. 42:657-665). These genes do not require ABA for their expression, but do respond to exogenous ABA.

There are also drought inducible genes that do not respond to ABA treatment. These include rd 21, erd1, and rd 19 that code for thiol proteases, CIp protease and thiol protease, respectively (Shinozaki, K. and Yamaguchi-Shinozaki, K. (1997) Gene expression and signal transduction in water-stress response. Plant Physiol. 115:327-334). Indeed, the information on such genes is very scarce.

There is always a need and search for novel drought related genes so that better adaptation may be sought. Apart from the genes and gene sequences listed in the Table 1, the novel gene sequences may be listed as follows:

ABRE. ABA-responsive element (PyACGTGGC; SEQ ID NO: 9) (Shen Q and Ho (1995) Functional Dissection of an Abscisic Acid (ABA)-Inducible gene Reveals Two Independent ABA-Responsive Complexes Each Containing a G-Box and a novel cis-Acting Element. The Plant Cell. 7:295-307).

G-box, ubiquitous regulatory elements (CACGTG; SEQ ID NO: 10). (Menkens, A. E., Schindler, U. and Cashmore A. R. (1995) The G-box: ubiquitous regulatory DNA element in plants bound by GBF family of bZIP proteins. Trends in Biochem Sci. 20:506-510).

DRE, Dehydration-responsive element (TACCGACAT; SEQ ID NO: 11) (Shinozaki, K. and Yamaguchi-Shinozaki, K. (1996) Molecular responses to drought and cold stress. Current opinion in biotechnology. 7:161-167). MYBRS, MYB recognition sequence (PyAACPyPu; SEQ ID NO: 12) (Urao T, Yamaguchi-Shinozaki K, Urao S, Shinozaki K (1993) An Arabidopsis myb homolog is induced by dehydration stress and its gene product binds to the conserved MYB recognition sequence. The Plant Cell 5:1529-1539).

MYCRS, MYC recognition sequence (CANNTG; SEQ ID NO: 13) (Abe, H., Yamaguchi-Shinozali, K., Urao, T., Iwasaki, T., Hosokawa, D and Shinozaki, K. (1997) Role of Arabidopsis MYC and MYB Homologs in Drought- and Abscisic Acid-Regulated Gene Expression. The Plant Cell. 9: 1859-1868).

While working with gene(s) and gene fragments (gene fragment in context to the present invention refers to partial nucleotide sequences of the complete gene), related to drought or other stresses, the following are possibilities:

(a) Gene can be Cloned Through Several Routs as Shown Below in Table 1.

TABLE 1

| Route/Technique Used | Reference |
|---|---|
| Protein sequencing followed by oligo-nucleotide synthesis and screening | Weretilnyk, E. A. and Hanson, A. D. 1990. Molecular cloning of a plant betenin oldohydo dehydrogenase, an enzyme implicated in soaptation to salinity and drought Prod. Notl. Acad. Sci. IISA 87: 2745-2749. |
| Plaque hybridization | Nakashima, k. Shinwari, Z. K., Sakuma, Y., Seki, M., Miura, S., Shipozaki, K and Yamaguchi-Shinozaki, K. 2000. Organization and expression of two Arapldopsts DRED2 genes eneeding DRE binding proteins involved in dehydration and high salinity responsive gene expression Plant. Mol. Biol. 42. 657-665. |
| PCR based cloning | Hirayama, T., Ohto, C., Mizoguchi, T., and Shinozaki, K. 1995. A gene encoding a phosphoinositol-specific phospholipase C in induced by dehydration and salt stress in *Arabidopsis thaliana* Proc. Natl Acad. Sci. 92: 3903-3907 |
| Library screening using heterologous probe | Richard, S., Morency, M., Drevet, C., Jouanin, L., and Seguin, S. 2000. Isolation and characterization of a dehydrin gene from white spruce induced upon wounding, drought and cold stress. Plant Mol. Biol. 43: 1-10. |
| Gene cloning using heterologous probe | Roberts, J. K. and Key, J. L. 1991. Isolation and characterization of a soybean hsp 70 gene. Plant molecular biology, 16: 671-683. |
| Differential Screening | Chang, S., Puryear, J. D., Dias, A. A. D. L, Funkhouser, E. A., Newton, R. J., and Calway, J. 1996. Gene expression under |

TABLE 1-continued

| Route/Technique Used | Reference |
|---|---|
| | water dificit in lobiolly pine (*Pinus taeda*): isolation and characterization of cDNA clones. Physiol. Plant. 97: 139-148. |
| Microarray | Seki, M., Nerusaka, M., Abe, H., Kasuga, M., Yamaguchi-Shinozaki, K., Caminci, P. Hayashizaki, Y., and Shinozaki, K. 2001 Plant Cell 113: 61-72 |
| Subtractive hybridization | a. Lee, S. W., Tomasetto, C., and Sagar R, 1991. Positive selection of fumous suppression genes by subtractive hybridization Proc. Nati Acad. Sci. USA, 88: 2825-2829.<br>b. Buchanan-Wollaston, V. and Ainaworth, C, 1997 Leaf senescence in *Brassica naus* cloning of senescence related gene bu substractive hybridication Plant Mol. Biol. 33, 821-834. |

(b) Gene Cloned from Organisms can be Expressed in Other Organisms.

As has been shown by Kishor, Kavi. P. B. R. Hong, Z., Miao, G. H., Hu, C. A. and Verma, D. P. S. (1995 Overexpression fo pyrroline-5-carboxylate synthetase increases proline production and confers osmotalerence in transgenic plants. Plant Physiol. 108:1387-1394 and the references therein) that the gene pyrroline-5-carboxylase synthetase was cloned from *Vigna aconotifolia* and expressed into tobacco through transgenic technology Transgenic tobacco plants were more tolerant under water stress conditions.

Pilon Smits, E. A. H., Ebskamp. M. J. M., Paul, M. J. Jeuken, M. J. W., Weisbeek, P. J. and Smeekens. Improved performance of transgenic fructan-accumulating tobacco under drought stress. Plant. Physiol. 107:125-130) transferred SacB gene from *Bacillus subtilis* into tobacco and found increased drought tolerance.

Holmstrom, K. O., Welin, B. and Mandal, A. (1994, Production of the *Escherichia coli* betaine-aidehyde sakydrogonase an enzyme required for the synthesis of the osmoprotectant glycine betaine, in transgenic plants. Plant J. 6:749-758) transferred betaine-aldehyde dehydrogenase from *Escherichia coli* (a microorganism) into tobacco (higher plant) and found to be drought tolerant.

(c) Genes Expressed in Response to Drought Stress can be Expressed by Other Environmental Variables as Well.

Iuchi, S., Kobayashi, Yamaguchi-Shimuzaki, K and Shinozaki, Kazuo (2000 A stress-inducibe gene for 9-cis-epoxycarotenoid dioxygenase involved in abscisic acid biosynthesis under water stress in drought tolerant compound. Plant physical 123:553-662) reported the expression of VcNCED1 in response to water and salt stress.

Pelloux J., Jolivet, Y., Hontaine, V., Banvoy, J., and Dizengromel, P. (2001 Changen in Rubieco and Rubisco activase gene expression and polypeptide expression.

Richard. S. Mordancy. M. Drevet. C. Jouanin, L. and Seguin, S. (2000. Isolation and characterization of a dehydrin gene from white spruce induced upon wounding, drought and cold stress. Plant Mol. Biol. 43: -1-10} reported a gene PgDhnl. which was induced In repose to drought, cold stress and upon wounding.

Nakashima. K. Shinwari, Z. K. Sakuma, Y. Seki. M. Miura, S, Shinozaki, K. and Yamaguchi-binozaki K. (2000 Organization and expression of two Arabidopsis DREB2 genes encoding DRE-binding proteins involved in dehydration and high salinity responsive gene expression. Plant. Mol, Biol 42; 657-665) reported the expression of drought responsive element DREB2 genes in response to dehydration and high salinity stress.

Hirayama. T. Ohto. C. Mizoguchi. T. and Shinozaki, K. (1995. A gene encoding a phosphoinositol-specific phospholipase C in induced by dehydration and salt stress in *Arabidopsis thaliano*, Proc. Natl. Acad. Sci 92: 3903-3907) reported expression of phosphoinosltol-specific phospholipase C in response to drought, salinity and low temperature.

Weretilnyk. E. A., and Hanson. A. D. (1990. Molecular cloning of a plant betaine-aldehyde dehydrogenase, an enzyme implicated in adaptation to salinity and drought. Proc. Natl. Acad. Sci., USA, 87: 2745-2749) reported the expression of betaine-aldehyde dehydrogenase gene in response to drought as well salinity, D. Identified Gene may be Used to Study Regulatory Elements. Regulatory Elements in Context to Present Invention Relate to the Regions such as Promoters, Transcriptional Factors and Other Sequences which Control the Expression of the Gene.

Using stress regulated gene HVA1. Straub, P. P. Shen Q. and Ho, Tuan-hua. D. (1994. Structure and promoter analysis of an ABA- and stress-regulated barley gene, HVA1. Plant. Mol. Biol. 26: 617-630) analysed promoter of the gene, Michel, D., Salamini F., Bartels, D. Dale, P., Baga, M. and szalay, A. (1993. Analysis of a desiccation and ABA-responsive promoter Isolated from the resurrection plant *Craterostigma plantagineum* Plant Journal 4: 29-40) selected drought responsive gene CdeT27-46 and analysed its promoter region.

Urao T, Yamaguchi-Shinozaki K. Urao S. Shinozaki K. (1993. An Arabidopsis myb homolog is induced by dehydration stress and its gene product binds to the conserved MYB recognition sequence. Plant Cell 5: 1529-1539) identified the sequences encoding transcription factors in a dehydration responsive gene Atmyb2 Yamaguchi-Shinozaki. K. and Shinozaki, K. (1997, Characterization of the expression of a desiccation-responsive rd29 gene of *arabidopsis thaliana* and analysis of its promoter in transgenic plants. Mol Gen Genet 236: 331-340) analysed the promoter region of a drought inducible gene rc(29.

Abe. H., Yamaguchi-Shinozaki. K. Urao, T. Iwasaki, T. Hosokawa. D and Shinozaki. K. (1997. Role of Arabidopsis MYC and MYB Homologs in Drought- and Abscisic Acid-Regulated Gene Expression. The Plant Cell.9: 1859-1868) analysed a drought inducible gene rd22 for regulatory factors.

Shen Q and Ho T. D. (1995. Functional Dissection of an Abscisic Acid (ABA)-Inducible gene Reveals Two Independent ABA-Responsive Complexes Each Containing a G-Box and a novel c/s-Acting Element. The Plant Cell. 7: 295-307) analysed HVA22 gene for regulatory elements and reported novel coupling elements.

e. Gene or Gene Fragment Isolated from One System can be Used as a Probe to Study the Similar Genes in Other Plant Systems Roberts, J K and Key. J. L. (1991. Isolation and characterization of a soybean hsp70 gene. Plant molecular biology, 16: 671-683) used hsp70 gene cloned from *Drosophila* to clone the similar gene from soybean.

Singia. S. L. Pareek A and Grover. (1997 Yeast HSP104 homologue rice HSP 110 is developmental- and stress regulated Plant science, 125: 211-219) showed that yeast hsp KM and rice hsp 110 are very similar. These are expressed in response to desiccation, salinity, low temperature and high temperature.

Shen, Q. Chen, C. N. Brands. A. Pan. S. M. and Ho, T. D. (2001 The stress- and abscisic acid-induced barley gene HVA 22: developmental regulation and homologues in diverse organisms. Plant Molecular Biology. 45: 327-340) reported a drought inducible gene HVA 22 in several organisms such as cereals, arabidopsis. *Caenorhabitis elegans*. man. mouse, and yeast.

(f) Gene Expressed in One Organ can be Expressed in Organ as Well as Shown Below in Table 2:

TABLE 2

| Organ | Reference |
|---|---|
| Roots and leaves | Nemoto, Y., Kawakami, N., and Sasakuma. 1999. Isolation of novel early salt-responding genes from wheat (*Triticum aestivum* L.) by differential display. Theor. Appl. Genet 98: 673-678<br>Thompson, A. J., Jackson, A. C., Parker, R. A., Morpeth, D. R., Burbidge, A. and Taylor, I. B. (2000) Abscisic acid biosynthesis in tomato: regulation of dioxygenase mRNA by light/dark cycles, water stress and abscisic acid. Plant.Mol.Biol. 42: 833-845 |
| Sheaths and roots | Claes, B., Dekkkeyser, R., Villarroel, R., Bulcke, M. V. D., Bauw, G., Montagu, M. V., and Caplan, A. 1990. Characterization of a rice gene showing organ specific expression in response to salt stress and drought. Plant Cell, 2: 19-27. |
| Stem Tissue and partially expanded vegetative buds, reproductive buds | Richard, S., Morency, M., Drevet, C., Jouanin, L., and Seguin, S. 2000. Isolation and characterization of a dehydrin gene from white spruce induced upon wounding, drought and cold stress, Plant Mol. Biol.43: 1-10 |

(g) It is possible to Clone Full Length cDNAs or Genomic DNA by Using Standard Protocols as detailed by Ausubel. F. M. Brend R. Kingston. R. E., Moore. D. D. Seidman. J. G. Smith, J. A., Struhl. K. 1987. Current protocols in molecular biology. Publisher John Wiley and Sons. New York: and Sambrook. J. Fritsch, E. F, and Maniatis. T. 1989. Molecular cloning; a laboratory manual, Second edition. Cold Spring Harbor Laboratory, Cold Spring Harbor, N.Y.

A summary of various drought-related genes is given below in Table 3.

TABLE 3

List of drought related genes along with their source and the predicted function.

| GENES | Predicted role/Homology | Species from which isolated | REFRENCE |
|---|---|---|---|
| A1494 | Cysteine thiol protease | *Arabidopsis thaliana* | Williams et al., 1994 Plant Mol. Biol. 25: 259-270 |
| ADH | Alcohol dehydrogenase | " | de Bruxelles et al., 1996 Plant Physiol. 111: 381-391; Dolferus et al., 1994 Plant Physiol. 105: 1075-1087; Jarillo et al., 1993 Plant Physiol. 833-837 |
| Athb-7 | Homeodomain leucine zipper transfactor | " | Söderman et al., 1996 Plant Journal 10: 375-381 |

TABLE 3-continued

List of drought related genes along with their source and the predicted function.

| GENES | Predicted role/Homology | Species from which isolated | REFRENCE |
|---|---|---|---|
| Athb-12 | Homeodomain leucine zipper transfactor | " | Lee and Chun, 1998 Plant Mol. Biol. 37: 377-384 |
| AthH2 | Aquaporin | " | Kaldenhoff et al., 1993 Plant Mol. Biol. 23: 1187-1198 |
| AthK1 | Histidine kinase | " | Urao et al., 1998 FEBS Left. 427: 175-178 |
| CDPK1/K2 | Cal dependent protein kinase | " | Urao et al., 1994 Mol. Gen. Genet. 244: 331-340 |
| HSP70-1/ERD2 | HSP-cognate | " | Kiyosue et al., 1994 Plant Mol. Biol. 25: 791-798 |
| HSP81-2/ERD8 | HSP-cognate | " | Kiyosue et al., 1994 Plant Mol. Biol. 25: 791-798 |
| rd22 | Unidentified seed protein of Vicia faba | " | Yamaguchi-Shinozaki and Shinozaki., 1993 Mol. Gen. Genet. 238: 17-25 |
| RAB18 | Dehydrin | " | Lang et al., 1994 Plant Physiol. 104: 1341-1349; Lang and Palva, 1992 Plant Mol. Biol. 20: 951-962 |
| RD19 | Cysteine protease | " | Koizumi et al., 1993 Gene 129: 175-182 |
| RD28, RD21 | Cysteine protease | " | Yamaguchi-Shinozaki et al., 1992 Plant Cell Physiol. 33: 217-224 |
| rd29A, rd29B | Drought responsive promoter element, drought related genes | " | Iwasaki et al., 1997 Plant Physiol. 115: 1287; Wang et al., 1995 Plant Mol. Biol. 28: 605-617 |
| DREB1A | Dehydration responsive elements binding proteins | " | Kasuga et al, 1999 Nature Biotechnology. 17: 287-291 |
| Tps1 | Trehalose biosynthesis | " | Holmstrom et al., 1994 Plant Journal 6: 749-758 |
| RPK1 | Receptor-like protein kinase | " | Hong et al., 1997 Plant Physiol 113: 1203-1212 |
| cAtP5CS | $\Delta^1$-pyrroline-5-carboxylate synthetase | " | Yoshiba et al., 1995 Plant J. 7: 751-760 |
| rd19A; rd21A | Cysteine proteases | " | Koizumi et al., 1993 Gene 129: 175-182 |
| UBQI | Ubiquitin extension protein | " | Kiyosue et al., 1994 Plant Mol. Biol. 25: 791-798 |
| cATCDPK1; cATCDPK2 | $CA^{2+}$-dependent, calmodulin-independent protein kinases | " | Urao et al., 1994 The Plant Cell 5: 1429-439 |
| cAtPLC1 | Phosphatidylinositol-specific phospholipase C | " | Hirayama et al., 1995 Proc. Natl. Acad. Sci. USA 92: 3903-3907 |
| ERD11; ERD13 | Glutathione S-transferases | " | Kiyosue et al., 1993. Biochem. Biophys. Res. Comm. 196: 1214-1220 |
| cAtsEH | Soluble epoxide hydrolase | " | Kiyosue et al., 1994 Plant J. 6: 259-269 |

TABLE 3-continued

List of drought related genes along with their source and the predicted function.

| GENES | Predicted role/Homology | Species from which isolated | REFRENCE |
|---|---|---|---|
| kin2 | Similarity to animal antifreeze proteins | " | Kurkela & Borg-Franck 1992 Plant Mol. Biol. 29: 689-692 |
| pA1494 | Similarity to proteases | " | Williams et al., 1994 Plant Mol. Biol. 25: 259-270 |
| ERD1 | Similar to a Clp ATP-dependent protease subunit | " | Kiyosue et al., 1993 Biochem. Biophys. Res. Comm. 196: 1214-1220 |
| Athsp70-1 | Similar to the HSP70 heat-shock-protein family | " | Kiyosue et al., 1994 Plant Mol. Biol. 25: 791-98 |
| Athsp81-2 | similar to the HSP81 heat-shock protein family | " | Kiyosue et al., 1994 Plant Mol. Biol. 25: 791-98 |
| rd22 | Similar to an unidentified seed protein from Vicia faba | " | Iwasaki et al., 1995 Mol. Gen. Genet. 247: 391-398 |
| lti65, lti78 | Unknown | " | Nordin et al., 1993 Plant Mol. Biol. 21: 641-653 |
| pRABAT1 | D11 LEA-protein related | " | Lang & Palva, 1992 Plant Mol. Biol. 20: 951-962 |
| Atmyb2 | MYB-protein-related transcription factor | " | Urao et al., 1993 The Plant Cell 5: 1429-1439 |
| ERD10; ERD14 | D11 LEA-protein related | " | Kiyosue et al., 1994 The Plant Cell Physiol. 35: 225-231 |
| SacB | Fructosyl transferase | *Bacillus subtilis* | Pilon-Smits et al., 1995 Plant Physiol. 107: 125-130 |
| MC12 | LKR/SDH cDNA of A. thliana | *Brassica napus* | Deleu et al., 1999 Plant Cell and Environment 22: 979-988 |
| MC43 | His-3 linker protein/ribosomal protein S12 | " | Deleu et al., 1999 Plant Cell and Environment 22: 979-988 |
| pBN115 | Similar to polypeptides encoded by pBN19 and pNB26 (*B. napus*), and COR15 (*A. thaliana*) | *Brassica napus* | Weretilnyk et al., 1993 Plant Physiol. 101: 171-177 |
| BnD22 | Similar to protease inhibitors | *Brassica napus* | Downing et al., 1992 Plant J. 2: 685-693 |
| VuNCED1 | ABA biosynthesis | Cowpea | Iuchi et al., 2000 Plant Physiol. 123: 553-562 |
| GapC-Crat | Cytosolic glyceraldehyde 3-phosphate dehydrogenase | *Craterostigma plantagineum* | Velasco et al., 1994 Plant Mol. Biol. 26: 541-546 |
| pSPS1 | Sucrose-phosphate synthase | " | Ingrams & Bartels, 1996 Annu Rev Plant Physiol 47: 377-403 |
| PSS1; pSS2 | Sucrose synthases | " | Ingrams & Bartels, 1996 Annu Rev Plant Physiol 47: 377-403 |
| pcC 37-31 | Similar to early-light-inducible proteins | " | Bartels et al., 1992 EMBO J. 11: 2771-2778 |
| pcC 13-62 | Unknown | " | Piatkowski et al., 1990 Plant Physiol. 94: 1682-1688 |

TABLE 3-continued

List of drought related genes along with their source and the predicted function.

| GENES | Predicted role/Homology | Species from which isolated | REFRENCE |
|---|---|---|---|
| pcC 27-04 | D11 LEA-protein related | " | Piatkowski et al., 1990 Plant Physiol. 94: 1682-1688 |
| pcC 6-19 | D11 LEA-protein related | " | Piatkowski et al., 1990 Plant Physiol. 94: 1682-1688 |
| pcC 3-06 | D7 LEA-protein related | " | Piatkowski et al., 1990 Plant Physiol. 94: 1682-1688 |
| pcC 17-45 | D95 LEA-protein related | " | Piatkowski et al., 1990 Plant Physiol. 94: 1682-1688 |
| pcECP40 | D11 LEA-protein related | *Daucus carota* | Kiyosue et al., 1993 Plant Mol. Biol. 21: 1053-1068 |
| Bet B | Glycine betaine biosynthesis | *Escherichia coli* | Holmstrom el al., 1994 Plant Journal 6: 749-758 |
| pTS.6 | Plasma membrane $H^+$-ATPase | *Glycine max* | Surowy and Boyer, 1991 Plant. Mol. Biol 16: 251-262 |
| SC514 | Lipoxygenase | " | Bell and Mullet 1991 Mol. Gen. Genet. 230: 456-462 |
| Ha hsp17.6Ha hsp17.9 | Low-molecular-weight heat-shock proteins | *Helianthus annuus* | Coca et al., 1994 Plant Mol. Biol. 25: 479-492 |
| Ha ds 10 | D19 LEA-protein related | " | Almoguera and Jordano 1992 Plant Mol. Biol. 19: 781-792 |
| Ha ds11 | D113 LEA-protein related | " | Almoguera and Jordano, 1992 Plant Mol. Biol. 19: 781-792 |
| B8; B9; B17 | D11 LEA-protein related | *Hordeum vulgare* | Close et al., 1989 Plant Mol. Biol. 13: 95-108 |
| B19.1; B19.3; B19.4 | D19 LEA-protein related | " | Espelund et al., 1992 The Plant Cell Environ. 18: 943-949 |
| HVA22 | LEA (Lateembryogenesis-abundant) and RAB (responsive to ABA) | " | Shen et al., 2001 Plant Mol. Biol. 45: 327-340 |
| BLT4 | Similar to protease inhibitors | " | Dunn et al., 1991 Mol. Gen. Genet. 229-389-394 |
| pBAD | Betaine aldehyde dehydrogenase | *Hordeum vulgare* | Ishitani et al., 1995 Mol. Gen. Genet. 247: 391-398 |
| pcht28 | Acidic endochitinase | *Lycopersicon chilense* | Chen et al., 1994 Mol. Gen. Genet. 145: 195-202 |
| SAM1; SAM3 | S-adenosyl-L-methionine synthetases | *Lycopersicon esculentum* | Espartero et al., 1994 Plant Mol. Biol. 25: 217-227 |
| P31 | Cytosolic copper/zinc superoxide dismutase | " | Perl-Treves and Galun 1991 Plant Mol. Biol. 17: 745-760 |
| TSW12 | A lipid transfer protein | " | Torres-Schumann et al., 1992 Plant Mol. Biol. 18: 749-757 |
| pLE16 | Similar to lipid transfer proteins | " | Plant et al., 1991 Plant Physiol. 97: 900-906 |
| pLE4 | D11 LEA-protein related | " | Cohen et al., 1991 Plant Physiol. 97: 1367-1374 |
| pUM90-1 | Similar to MsaciA and pSM2075 polypeptides | *Medicago sativa* | Luo et al., 1992 J. Biol. Chem. 267(22): 15367-15374 |
| pSM1075 | Similar to MsaciA and pUM90-1 polypeptides | " | Luo et al., 1991 Plant Mol. Biol. 17: 1267-1269 |

TABLE 3-continued

List of drought related genes along with their source and the predicted function.

| GENES | Predicted role/Homology | Species from which isolated | REFRENCE |
|---|---|---|---|
| MsaciA | Similar to pUM90-1 and pSM2075 polypeptides | " | Laberge et al., 1993 Plant Physiol. 101: 1411-1412 |
| pPPC1 | Phosphoenolpyruvate carboxylase | *Mesembryanthemum crystallinum* | Vernon et al., 1993 The Plant Cell Environ. 16: 437-444 |
| pRAB 16A | D11 LEA-protein related | *Oryza sativa* | Mundy & Chua 1988. EMBO J. 7: 2279-2286 |
| salT | Unknown | " | Claes et al., 1990 The Plant Cell 2: 19-27 |
| Apx1 gene | Cytosolic ascorbate peroxidase | *Pisum sativum* | Mittler and Zilinskas 1994 Plant J. 5: 397-405 |
| Sod 2 gene | Cytosolic copper/zinc superoxide dismutase | " | White and Zilinskas 1991 Plant Physiol. 96: 1291-1292 |
| 26g | Some similarity to aldehyde dehydrogenase | " | Guerrero et al., 1990 Plant Mol. Biol. 15: 11-26 |
| 7a | Similar to channel proteins | " | Guerrero et al., 1990 Plant Mol. Biol. 15: 11-26 |
| 15a | Similarity to proteases | " | Guerrero et al., 1990 Plant Mol. Biol. 15: 11-26 |
| pLP2 | S-Adenosyl methionine synthatase | *Pinus taeda* | Chang et al., 1996 Physiol. Plant. 97: 139-148 |
| pLP3 | Silk fibrion and rat chondroitin core protein | " | Chang et al., 1996 Physiol. Plant. 97: 139-148 |
| pLP4 | Tomato protein TMA SN1(water deficit inducible) | " | Chang et al., 1996 Physiol. Plant. 97: 139-148 |
| pLP5 | Copper binding protein | " | Chang et al., 1996 Physiol. Plant. 97: 139-148 |
| P22 | Similar to protease inhibitors | *Raphanus sativus* | Lopez et al., 1994 Physiol. Plant. 91: 605-614 |
| H26 | D11 LEA-protein related | *Stellaria longipes* | Robertson and Chandler 1992 Plant Mol. Biol. 19: 1031-1044 |
| pMA2005 | D71 LEA-protein related | *Triticum aestivum* | Curry et al., 1991 Plant Mol. Biol. 16: 1073-1076 |
| pMA1949 | D7 LEA-protein related | " | Curry & Walker-Simmons 1993 Plant Mol. Biol. 21: 907-912 |
| Em | D19 LEA-protein related | " | Litts et al., 1987 Nucleic Acids Res. 15: 3607-3618 |
| PKABAI | Protein kinase | " | Aderberg and Walker-Simmons 1992 Proc. Natl. Acad. Sci. USA 89: 10183-10187 |
| Pmbm1 | L-isoaspartyl methyltransferase | " | Mudgett & Clarke 1994 J.Biol.Chem.269: 25605-25612 |
| M3 (RAB-17) | D11 LEA-protein related | *Zea mays* | Close et al., 1989 Plant Mol. Biol. 13: 95-108 |
| pMAH9 | Similar to RNA-binding proteins | " | Gómez et al., 1988 Nature 334: 262-264 |

Below is specifically given a state of art knowledge with reference to cloning of drought stress related genes.

Reference may be made to document (1) by Yamaguchi-Shinozaki, K. and Shinozaki, K. (1994) The Plant Cell. 6: 251-264, wherein is described the identification of a novel cis-acting element involved in responsiveness to drought, low temperature; or high salt stress from a model plant *Arabidopsis*.

Reference may be made to document (2) by Li, L. g., Li, S. f., Tao, Y., and Kitagawa, Y. (2000) Plant Science 154: 43-51, wherein a novel water channel protein was cloned from rice which was shown to be involved with the chilling tolerance in *Xenopus oocytes*.

Reference may be made to document (3) by Tabaeizadeh; Zohrer,; Yu; Long-Xi; Chen; Ri-Dong, U.S. Pat. No. 5,656,474 dated Aug. 12, (1997) wherein two osmotic stress- and ABA-responsive members of the endochitinase gene family were isolated and identified from the leaves of drought-stressed *Lycopersicon chilense* plants.

Reference may be made to document (4) by Kim; Soo Young U.S. Pat. No. 6,245,905 dated Jun. 21, (2001) wherein a nucleic acid molecule encoding the Abscisic acid responsive element binding factor 2 (ABF2) was isolated that binds abscisic acid responsive elements in plants.

Reference may be made to document (5) by Kim; Soo Young U.S. Pat. No. 6,218,527 dated Apr. 17, (2001) wherein a nucleic acid molecule encoding the Abscisic acid responsive element binding factor 3 (ABF3) was isolated that binds abscisic acid responsive elements in plants.

Reference may be made to document (6) by Thomshow; Michael F.; Stockinger; Eric, J. U.S. Pat. No. 5,892,009 dated Apr. 6, 1999 wherein a gene designated as CBF1, encoding a protein CBF1, which binds to a region regulating expression of gene which promote cold temperature and dehydration tolerance in plants was cloned.

Reference may be made to document (7) by Chun; Jong-Yoon; Lee; Yong-Hun. U.S. Pat. No. 5,981,729 dated Nov. 9, 1999 wherein a novel gene induced by water deficit and abscisic acid was cloned.

The Drawbacks in the Prior Art are:
a. Earlier work to clone the genes related to drought stress focused on model plant system and mainly annuals. Perennial evergreen plants such tea experience several rounds of drought stress during their life cycle. The plant is, therefore, expected to harbor novel gene(s) imparting tolerance to drought.
b. There is always search of novel genes so as to exploit it for generating more drought tolerant plants. Model plants such as Arabidopsis thaliana and other domesticated plants as mentioned in Table 1 have been used to clone the drought-related genes. Novel genes can be expected from a hitherto unstudied plant.
c. Methods reported to clone drought related gene relied on differential screening of cDNA library, analysis of differential cDNA library, and subtractive hybridization (Tables 1, 2 and 3). These have inherent limitation of using two samples at a time for analysis Therefore, after identification and cloning of differentially expressed genes, these used to be tested for their expression analysis during recovery and/or in response to other variables such as salt stress/ABA treatment etc. Therefore, appropriate technology needs to applied in order to focus on the desired gene at the beginning itself.

The above drawbacks have been eliminated for the first time in a simple and reliable manner by the present invention, which is not so obvious to the person skilled in the art.

OBJECTS OF THE PRESENT INVENTION

The main object of the present invention is the cloning of novel genes expressed in the leaves of tea plant experiencing drought stress.

Another main object of the present invention is the cloning of novel genes expressed in the leaves of tea plant experiencing drought stress while still attached to the whole plant.

Yet another object of the present invention is the identification of novel genes expressed in the leaves of tea plant experiencing drought stress.

Still another object of the present invention is the cloning of novel genes repressed in the leaves of tea plant experiencing drought stress.

Still another object of the present invention is to generate a spectrum of the gene(s) expressed and repressed in the leaves of tea plant experiencing drought stress versus the well-irrigation for the purpose of identification of differentially expressed genes and cloning thereafter.

Still another object of the present invention is to generate a spectrum of the gene(s) expressed and repressed in the 4$^{th}$ leaf of tea experiencing drought stress, ABA treatment, during recovery and under well-irrigated condition (well irrigated condition would mean the amount of water applied that allows the plant to maintain its water potential) for the purpose of identification of differentially expressed genes and cloning thereafter.

Further object of the present invention is to quantify the stress in terms of water potential.

Yet another object of the present invention is to study alterations in physiological activities in response to drought stress.

Still another object of the present invention is to determine the location of the variable region of genome in the drought-tolerant tea plants.

Still another object of the present invention is the confirmation of the identified 3' ends of the differentially expressed gene(s) for establishing differential expression in the leaves of tea plants experiencing drought stress compared to the well-irrigated tea plants.

Further object of the present investigation is the expression study of the identified gene in response to abscisic acid and during recovery. Recovery in context to the present invention refers when drought stressed plants are irrigated and their water potential equals the well-irrigated control plants.

Yet another object of the present invention is the cloning of the identified 3' ends of the differentially expressed gene(s).

Still another object of the present invention is the sequencing of the identified 3' ends of the cloned gene.

Still another object of the present invention is the comparison of the sequences of the cloned genes from the gene databank.

Further object of the present invention is to develop a method of introducing water-stress tolerance in biological systems using the said three novel genes.

Yet another object of the present invention is to develop a method of introducing water-stress tolerance in Tea plants using the said three novel genes.

SUMMARY OF THE PRESENT INVENTION

The present invention relates to three novel genes of SEQ ID Nos. 1-3 useful for water-stress tolerance in biological systems, wherein said genes are differentially expressed in Tea plant under drought conditions and a method of introducing said genes into a biological system to help develop water stress tolerance.

DETAILED DESCRIPTION OF THE PRESENT INVENTION

Accordingly, the present invention relates to three novel genes of SEQ ID Nos. 1-3 useful for water-stress tolerance in biological systems, wherein said genes are differentially expressed in Tea plant under drought conditions and a method of introducing said genes into a biological system to help develop water stress tolerance.

In one embodiment of the present invention, the three novel genes showing differential expression are as follows:

```
DS 31  (T11G,AP65) - SEQ ID NO.1
DS 61  (T11A,AP1)  ---SEQ ID NO.2
DS103  (T11A,AP65) - SEQ ID NO.3
```

Various primer combinations used to clone the genes are depicted inside the bracket. The details of these primers are mentioned in example 4.

DS 31 (T11G, AP65), which is basically a 3' end region of the gene, hybridized to the transcript of 1.5 kilobase size on northern blot as in FIG. 7.

DS 61 (T111A, API), which is basically a 3' end region of the gene, hybridized to the transcript of 750 base size on northern blot as in FIG. 7.

DS103 (T11A, AP 65), which is basically a 3' end region of the gene, hybridized to the transcript of 1.9 kilobase size on northern blot as in FIG. 7.

Each clone was sequenced manually using a T7 sequence version 2 sequencing kit from M/s. Amersham Pharmacia Biotech, USA. Sequencing primers used were [Lgh (5'-CGA-CAACACCGATAATC-3'; SEQ ID NO: 14) or Rgh (5'-GACGCGAACGAAGCAAC-3'; SEQ ID NO: 15)].

Further embodiment of the present invention, the sequence of said three genes is as follows:

INFORMATION FOR SEQ ID NO: 1
(i) SEQUENCE CHARACTERISTICS: (A) LENGTH: 318 base pairs
(B) TYPE: nucleic acid
(C) STRANDEDNESS: double (D) TOPOLOGY: circular
(ii) MOLECULE TYPE: cDNA
(iii) SEQUENCE DESCRIPTION: SEQ ID NO:1

```
                                           (SEQ ID NO:1)
aatcaatatt gttgcactca tgggcctggg atcatgtggg cctggatcat gtgggcctac acctttgtcc aagttcttca aggataggtg cccagatgct tatagctatc ctcaggatga tccaaccagt ttgttcactt gtcctcctgc tggtaccaat tattgcctat accttctgcc cttgaggcct cttttcact cccttccctc tctttataat tataggacag tgttatagta caataagacc tcactagttt caatatttgt gagattcaga cactgtgttt aattaaattt gtgacattta gtgttgtc
```

Gene number and details: DS 31 (T11G, AP65). The items mentioned inside the bracket depict primers combination. The detail of these primers is mentioned in Example 4.

Primer

```
                                          (SEQ ID NO:26)
aagc ttcaagacc aatcaatatt gttgcactca tgggcctggg atcatgtggg cctggatcat gtgggcctac acctttgtcc aagttcttca aggataggtg cccagatgct tatagctatc ctcaggatga tccaaccagt ttgttcactt gtcctcctgc tggtaccaat tattgcctat accttctgcc cttgaggcct cttttcact cccttccctc tctttataat tataggacag tgttatagta caataagacc tcactagttt caatatttgt gagattcaga cactgtgttt aattaaattt gtgacattta gtgttgtc ca aaaaaaaaaa gctt
```

INFORMATION FOR SEQ ID NO:2
(1) SEQUENCE CHARACTERISTICS: (A) LENGTH: 251 base pairs
(B) TYPE: nucleic acid
(C) STRANDEDNESS: double (D) TOPOLOGY: circular
(ii) MOLECULE TYPE: cDNA
(iii) SEQUENCE DESCRIPTION: SEQ ID NO:2

```
                                          (SEQ ID NO:2)
aataagaagg ggtcttgact agcccctgtt atatgagacg tgaggagcga tggcgatgac gatgatgacg atgatgatgt tggtgtggca gccagccgca taactttttt cagtttgat tgtctaaggt tttgatatgt taatggtcag ctaagcaaat acatgagctc atatattcag tacttggcat ataaataacc tgtcttgcta ttcatattaa tgttctagat atgataatca ccttctctct c
```

Gene number and details: DS 61 (T11A, AP1) The items mentioned inside the bracket depict primers combination. The detail of these primers is mentioned in Example 4.

Primer

```
                                          (SEQ ID NO:27)
aagc ttgattgcc aataagaagg ggtcttgact agcccctgtt atatgagacg tgaggagcga tggcgatgac gatgatgacg atgatgatgt tggtgtggca gccagccgca taactttttt cagtttgat tgtctaaggt tttgatatgt taatggtcag ctaagcaaat acatgagctc atatattcag tacttggcat ataaataacc tgtcttgcta ttcatattaa tgttctagat atgataatca ccttctctct ctaaaaaaaa aaagctt
```

INFORMATION FOR SEQ ID NO:3
(i) SEQUENCE CHARACTERISTICS: (A) LENGTH: 361 base pairs
(B) TYPE: nucleic acid
(C) STRANDEDNESS: double (D) TOPOLOGY: circular
(ii) MOLECULE TYPE: cDNA
(iii) SEQUENCE DESCRIPTION: SEQ ID NO:3

(SEQ ID NO:3)
```
atcggcaaca gatgttgaaa ctcaccttac actaatgtgt ccagatcttc tcaacaggaa ttctagcaac cgaggacacc actatgatgt gtccagctct tctcaacagg aattgtagca atttagacaa ccgaggacac cactatacat acatacaagc atggttttaa ataaagcgtt cacatagctg atatcagata ctattgacgt gcagatattg ttgaatatcg gtatcaatat tttaaaacca tgcatatgag agttcaacac aagttagaag ctctcttttg ttttcatttt acaagtttgt gtaatttgat gtaagagcaa aagcttagta tatgtaatga gaattttgaa c
```

Gene number and details: DS103 (T11A, AP 65). The items mentioned inside the bracket depict primers combination. The detail of these primers is mentioned in example 4.

Primer (SEQ ID NO:28)
```
aagc ttcaggacc atcggcaaca gatgttgaaa ctcaccttac actaatgtgt ccagatcttc tcaacaggaa ttctagcaac cgaggacacc actatgatgt gtccagctct tctcaacagg aattgtagca atttagacaa ccgaggacac cactatacat acatacaagc atggttttaa ataaagcgtt cacatagctg atatcagata ctattgacgt gcagatattg ttgaatatcg gtatcaatat tttaaaacca tgcatatgag agttcaacac aagttagaag ctctcttttg ttttcatttt acaagtttgt gtaatttgat gtaagagcaa aagcttagta tatgtaatga gagttggaa c taaaaaaaa aaagctt
```

In one embodiment of the present invention, wherein genes of SEQ ID No. 1-3.

In another embodiment of the present invention, wherein gene of SEQ ID No.1 is of length 318 bp.

In yet another embodiment of the present invention, wherein gene of SEQ ID No. 2 is of length 251 bp.

In still another embodiment of the present invention, wherein gene of SEQ ID No. 3 is of length 361 bp.

In still another embodiment of the present invention, wherein said genes are circular in shape.

In still another embodiment of the present invention, wherein said genes are differentially expressed in tea plant (*Camellia sinensis* (L.) O. Kuntze) under water-deficient stress conditions.

In further embodiment of the present invention, a method of identifying genes of SEQ ID No. 1-3 differentially expressed in tea plant under water-deficient stress conditions.

In yet another embodiment of the present invention, isolating total mRNA from said plant growing both under normal and drought conditions.

In still another embodiment of the present invention, reverse transcripting said mRNAs to obtain corresponding cDNA.

In still another embodiment of the present invention, sequencing said cDNA.

In still another embodiment of the present invention, identifying differentially expressed genes using said cDNA sequences.

In still another embodiment of the present invention, wherein sequencing cDNA by dideoxy chain termination method.

In still another embodiment of the present invention, wherein reverse transcripting mRNA into cDNA by using enzyme reverse transcriptases.

In still another embodiment of the present invention, wherein said genes are differentially expressed in leaf of the tea plant.

In still another embodiment of the present invention, wherein said method shows differential expression at 3' end of mRNA strands of said plant.

In still another embodiment of the present invention, wherein tea plant is *Camellia sinensis* (L.) O. Kuntze.

In still another embodiment of the present invention, wherein said differential expression is confirmed by Northern blotting.

In further embodiment of the present invention, a method of introducing water-deficient stress tolerance in plant systems using genes of SEQ ID No. 1-3, said method comprising step of transferring said genes into the said systems.

In another embodiment of the present invention, wherein said genes are transformed using techniques selected from a group comprising *Agrobacterium* mediated transformation and Biolistic mediated transformation.

In another embodiment of the present invention, wherein said method is used to modulate said stress tolerance.

In still another embodiment of the present invention, wherein said genes are used to develop probes to identity plant systems with tolerance to grow under said water-deficient stress conditions.

In still another embodiment of the present invention, wherein said genes are used to develop tolerance under drought conditions.

In still another embodiment of the present invention, wherein said genes are used to develop tolerance against drought.

In further embodiment of the present invention, the said three novel genes of SEQ ID Nos. 1-3, wherein said genes are responsible for water stress tolerance in plants. The said genes are used independently or in combination to introduce drought tolerance in plants. The said genes are isolated from the leaves of tea plant.

In another embodiment of the present invention, the said genes are stable in plant systems. The genes are found to express themselves in all plant systems with help from its promoter and regulatory elements. The said genes are able to introduce drought tolerance in all plant systems. The drought tolerance is seen particularly in tea plants where said genes are incorporated.

In yet another embodiment of the present invention, the said genes are observed for their uniform expression in plant systems for ⅔ generations. The said gene expression was found to be uniform in ⅔ generations.

In further embodiment of the present invention, the said genes are found to exert no adverse effect on the normal functioning of the plant systems which are transformed with said genes.

In further embodiment of the present invention, cloning of novel genes expressed in leaves of *Camellia sinensis* (L.) O. Kuntze (hereinafter referred to as tea) experiencing drought stress. Particularly, this invention relates to the comparison of gene expression pattern in the 4$^{th}$ leaf of 2 year old tea plants growing under water stress versus the well irrigated tea plants with a view to identify and clone the differentially expressed gene(s). Particularly, this invention relates to identification, cloning and analysis of novel 3 prime (hereinafter referred to as 3') ends of the genes [gene within the present scope of invention refers to that part of deoxyribonucleic acid (hereinafter referred to DNA) that give rise to messenger ribonucleic acid (hereinafter referred to mRNA)] expressed in 4$^{th}$ leaf of tea plant experiencing drought stress. 3' end refers to that end that is very close to poly-A tail of mRNA.

In another embodiment of the present invention, Accordingly the present invention provides Cloning of 3 novel genes modulated under drought stress conditions in tea (*Camellia sinensis* (L.) O. Kuntze) which comprises:

novel gene sequence expressed in the 4$^{th}$ leaf of tea plants experiencing drought stress, novel gene sequences repressed in the 4$^{th}$ leaf of tea plants experiencing drought stress, spectrum of 3' ends of the expressed and repressed genes in the 4$^{th}$ leaf of tea plants for the purpose of identification of differentially expressed genes and cloning thereafter, confirmation of the identified 3' ends of the differentially expressed gene(s) for establishing differential expression in the tea plants, and sequence information of the cloned 3' ends of the differentially expressed gene(s)

In another embodiment of the present invention, 2 years old tea plants clone TV 78 growing in the experimental farm of the Institute of Himalayan Bioresource Technology, Palampur (32° 06' 32" N; 76° 33' 43" E; altitude 1300 m) were selected. All the plants were vegetatively propagated from the same mother plants that ensured genetic homogeneity of all the plants under study. Thus, the observed altered gene expression in response to a treatment will reflect the effect of treatment rather than the genetic heterogeneity. Plants were raised in plastic pots (14.5 cm height×15 cm top diameter×9 cm bottom diameter). One pot had only one plant.

In yet another embodiment all the plants were kept in a glass house to ensure uniformity in temperature and relative humidity. Fully expanded leaves at 4$^{th}$ node position from the top (average length, 9.5±0.19 cm; average width 3.65±0.1 cm) were used in all the experiments. While 1$^{st}$, 2$^{nd}$ and 3$^{rd}$ leaf would show alteration in leaf area during the experimentation period leading to growth related alteration in gene expression, the leaf area of 4$^{th}$ leaf remained constant with average length of 9.5±0.19 cm and average width of 3.65±0.1 cm throughout the experimentation period. Hence, the leaf at 4$^{th}$ node position was selected in the present invention. Leaf at 5$^{th}$ node position would be relatively older compared to the leaf at 4$^{th}$ node position. The whole strategy in the present invention was to select the leaf at node position, which should be relatively younger as well as where growth related alterations are negligible/minimal.

In still another embodiment control plants were watered regularly, whereas drought was imposed by withholding water in the treatment pots. ABA (5 mM) was applied at 2 days interval to both adaxial and abaxial surface with the help of cotton and also applied to the roots (2 ml) in the plants designated for ABA treatment. These were watered regularly as the control plants. For recovery experiments, drought was applied for 14 days and were watered thereafter.

In still another embodiment data recording for various parameters was performed on day 0, 7, 14 and 18 after giving the treatments. Leaf samples for differential display and northern analysis were collected on day 14 (for control, drought and ABA) and on day 18 (for recovery experiment).

Leaves were washed with diethyl pyrocarbonate (hereinafter known as DEPC) treated water [to prepare DEPC treated water, DEPC was added in distilled water to a final concentration of 0.1% followed by autoclaving (i.e. heating at 121° C. under a pressure of 1.1 kg per square centimeters) after an overnight incubation], harvested and immediately dipped in liquid nitrogen to freeze the cellular constituents for ceasing the cellular activities.

In still another embodiment this invention relates to identification, cloning and analysis of novel 3 prime (hereinafter called as 3') ends of the genes that are expressed in 4$^{th}$ leaf of tea experiencing drought stress.

In still another embodiment this invention relates to identification, cloning and analysis of novel 3' ends of the genes that are repressed in 4$^{th}$ leaf of tea experiencing drought stress.

In still embodiment of the present invention total RNA from CO, DS, RC and AB leaf was isolated and the "differential display technique" (Liang, P., Zhu, W., Zhang, X., Guo, Z., O'Connell, R., Averboukh, L., Wang, F. and Pardee, A. B. (1994). Differential display using one-base anchored oligo-dT primers. Nucleic Acids Res. 22(25): 5763-5764) was employed to generate a spectrum of 3' ends of the expressed and repressed genes in CO, DS, RC and AB leaf.

In further embodiment of the present invention, 3' ends of the expressed genes in DS buds of tea were ligated into a vector to yield a recombinant plasmid, which upon transformation into a suitable *E. Coli* host resulted into a clone. Vector, in the present invention refers to the sequence of DNA capable of accepting foreign DNA and take the form of a circular plasmid DNA that shows resistance to a given antibiotic.

In an advantageous embodiment of the present invention 3' ends of the repressed genes in DS buds of tea were ligated into a vector to yield a recombinant plasmid, which upon transformation into a suitable *E. coli* host resulted into a clone.

In yet another embodiment of the present invention the gene cloned was tested for its expression or repression in CO, DS, RC and AB leaf of tea to define association of the cloned gene with the drought stress.

In another embodiment of the present invention the gene was sequenced using the dideoxy chain termination method (Sanger, F. S., Nicklen, and A. R., Coulson (1977) DNA sequencing with chain-terminating inhibitors. Proc. Natl. Acad. Sci. USA74: 5463-5467) to figure out the uniqueness of the gene.

In further embodiment of the present invention, the said three novel genes of SEQ ID Nos. 1-3, wherein said genes are responsible for water stress tolerance in plants. The said genes are used independently or in combination to introduce drought tolerance in plants. The said genes are isolated from the leaves of tea plant.

In another embodiment of the present invention, the said genes are stable in plant systems. The genes are found to express themselves in all plant systems with help from its promoter and regulatory elements. The said genes are able to introduce drought tolerance in all plant systems. The drought tolerance is seen particularly in tea plants where said genes are incorporated.

In yet another embodiment of the present invention, the said genes are observed for their uniform expression in plant systems for ⅔ generations. The said gene expression was found to be uniform in ⅔ generations.

In further embodiment of the present invention, the said genes are found to exert no adverse effect on the normal functioning of the plant systems which are transformed with said genes.

BRIEF DESCRIPTION OF THE ACCOMPANYING DRAWINGS

FIG. 1 represents Water potential (A), photosynthesis rate (B) and Fv/Fm ratio (C) of $4^{th}$ leaf of 2 years old seedlings of tea plant subjected to ABA (AB) treatment, drought stress (DS) by withholding water and subsequently rewatered on day 14 (RC). Data are means±sd of four different measurements.

FIG. 2 represents Total RNA isolated from the $4^{th}$ leaf of tea plants. Abbreviations used in the figure carry the following meaning: CO, RNA isolated from well-irrigated control plants; DS, RNA isolated from drought-stressed plants; RC, RNA isolated from recovered plants; AB, RNA isolated from ABA treated plants. M represents RNA marker.

The present invention will be illustrated in greater details by the following examples. These examples are presented for illustrative purposes only and should not be construed as limiting the invention, which is properly delineated in the claims.

EXAMPLES

Example 1

Water Potential, Photosynthesis Rate and Fv/Fm Ratio of $4^{th}$ leaf of 2 Years Old Seedlings of Tea Plant Subjected to ABA (AB) treatment, Drought Stress (DS) by Withholding Water and Subsequently Rewatered on Day 14 (RC).

Water potential (hereinafter known as $\psi$) was measured using a psychrometer (dew point microvoltmeter; model HR 33T, Wescor, USA). Leaf disc (0.5 cm diameter) was punched using a sharp paper punch and was immediately kept in sample chamber (C-52; Wescor, USA). After 30 min of equilibration, the value was obtained in terms of cooling coefficient (units=micro-volts). The value was divided by 0.75 (proportionality constant to convert the values obtained into "bar", the unit of $\psi$) to obtain the value of $\psi$. The complete unit of psychrometer is calibrated for 25° C. For the measurements done at temperatures other than 25° C., the following formula was used to compensate for the temperature:

Cooling coefficient at new temperature=0.7 (new temperature in degree Celsius−25° Celsius)+standard value of cooling coefficient at 25° C. (given by the manufacturer) Photosynthesis rate was measured using a portable photosynthesis system (Li-6400, Li-COR, Lincoln, Neb., USA). Light intensity was kept constant at $1000\,\mu E\,m^{-2}\,s^{-1}$ using blue-red LED device supplied by the manufacturer and the chamber temperature was maintained at 25° C. using a Peltier cooling and heating device as supplied along the instrument.

Chlorophyll fluorescence induction kinetics parameters were measured using plant stress meter (PSM Mark II, Biomonitor, Sweden). Leaves were dark adapted for 30 min using dark adaptation clips before exciting chlorophyll using an actinic light with peak at 500 nm. Fv/Fm ratio, that shows the photochemical efficiency of photosystem II, was recorded as per the manufacturer's instructions.

Figure 1:
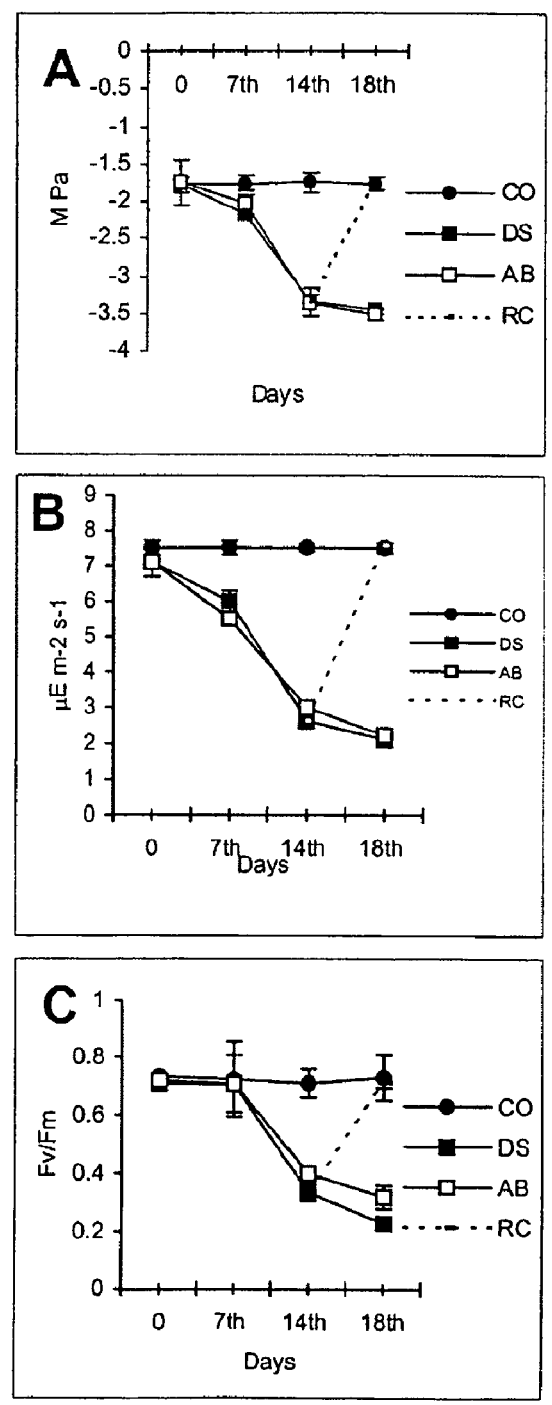

Phenotypically, the leaves of CO and RC plants were flat and open, whereas leaves of DS and AB plants showed partial leaf curling, a characteristic of plant response to drought. Parameters such as $\psi$, A and Fv/Fm remained constant throughout the experimentation period in control leaves (FIG. 1). Also, leaf area of the $4^{th}$ leaf was unaltered during the experimentation period in control plants.

In the pots wherein watering was withheld, $\psi$ dropped by 23.4% in 7 days time whereas in 14 days, the values dropped by 87.2%. For A, the value dropped by 15.5 and 62.9% and for Fv/Fm, values dropped by 0.56 and 52.5% on the above days. In case of ABA treatment, $\psi$ dropped by 16.5 and 52.5% in 7 and 14 days time, respectively. For A, the value dropped by 22.5 and 57.7% and for Fv/Fm, values dropped by 1.8 and 44.2% on the above days. Drop in values in all the above cases has been expressed in relation to day zero value (FIG. 1).

In recovery experiments, the values of $\psi$, A and Fv/Fm were quite similar to control plants.

The experiment thus showed remarkable ability of tea to revive to its normal function in terms of A, Fv/Fm and $\psi$ characteristic in spite of severe drought stress wherein $\psi$ was only 12.8% of its day zero value. Also, the data quantified gene expression pattern at a particular $\psi$.

Example 2

RNA Isolation, Digestion of RNA with DNase 1, Quantification of RNA and Gel-Electrophoresis:

To ensure a high quality of ribonucleic acid (hereinafter known as, RNA) from CO, DS, RC and AB leaf of tea, RNeasy plant mini kits (purchased from M/s. Qiagen, Germany) were used. Manufacturer's instructions were followed to isolate RNA. RNA was quantified by measuring absorbance at 260 nm and the purity was monitored by calculating the ratio of absorbance measured at 260 and 280 nm. A value >1.8 at 260/280 nm was considered ideal for the purpose of present investigation. The formula used to calculate RNA concentration and yield was as follows:

Concentration of RNA (µg/ml)=$A_{260}$ (absorbance at 260 nm)×40×dilution factor Total yield (µg)=concentration×volume of stock RNA sample To check the integrity of RNA, 5-6 µg of RNA in 4.5 µl of DEPC treated autoclaved water was diluted with 15.5 µl of M1 solution (2 µl of 5×MOPS buffer, 3.5 µl of formaldehyde, and 10 µl of formamide [5×MOPS buffer: 300 mM sodium acetate, 10 mM MOPS (3-{N-morpholino]propanesulfonic acid}, 0.5 mM ethylene diamine tetra-acetic acid (EDTA)] and incubated for 15 minutes at 65° C. RNA was loaded onto 1.5% formaldehyde agarose-gel after adding 2 µl of formaldehyde-gel loading buffer [50% glycerol, 1 mM EDTA (pH, 8.0), 0.25% bromophenol blue, 0.25% xylene cyanol FF], and electrophoresed at 72 volts in 1×MOPS buffer (60 mM sodium acetate, 2 mM MOPS, 0.1 mM EDTA), following Sambrook, J., Fritsch, E. F. and Maniatis, T. 1989 (Molecular Cloning: A Laboratory Manual, Cold Spring Harbor Laboratory Press, Plainview, N.Y.).

Figure 2:
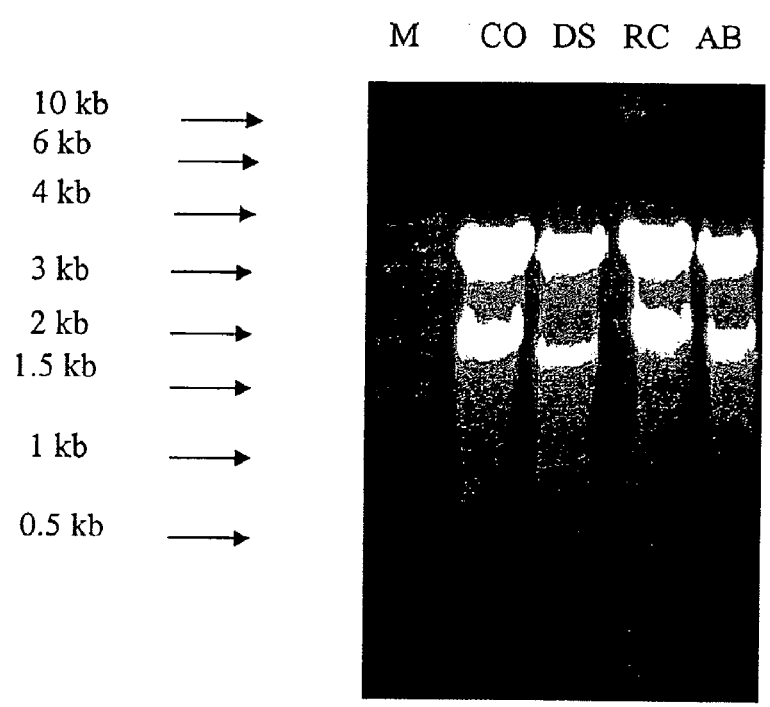

To remove the residual DNA, RNA (10-50 µg) was digested using 10 units of DNase I, in 1× reaction buffer [10× reaction buffer: 100 mM Tris-Cl (pH, 8.4), 500 mM KCl, 15 mM MgCl$_2$, 0.01% gelatin] at 37° C. for 30 minutes (Message Clean Kit from M/s. GenHunter Corporation, USA). DNase I was precipitated by adding PCI (phenol, chloroform, isoamylalcohol in ratio of 25:24:1) and RNA present in the aqueous phase was precipitated by adding 3 volumes of ethanol in the presence of 0.3 M sodium acetate. After incubating for 3 hours at −70° C., RNA was pelleted, rinsed with chilled 70% ethanol and finally dissolved in 10 µl of RNase free water. DNA-free-RNA thus obtained was quantified and the integrity was checked as above. The quality of RNA is depicted in FIG. 2.

When needed large quantity of RNA, we used the modified guanidine hydrochloride based procedure (Lal, L., Sahoo, R., Gupta, R. K., Sharma, P. and Kumar, S. Plant Molecular Biology Reporter 19:181a-181f).

Apart from these two, the other procedure can also be used to isolate RNA from the 4$^{th}$ leaf of tea.

Example 3

Conversion of mRNA into Complementary DNAs (Hereinafter Referred to cDNAs) by Reverse Transcription (Hereinafter Referred to RT):

0.2 µg of DNA-free-RNA from CO, DS, RC and AB samples was reverse transcribed in separate reactions to yield cDNAs using an enzyme known as reverse transcriptase. The reaction was carried out using 0.2 µM of T$_{11}$M primers (M in T$_{11}$M could be either T$_{11}$A, T$_{11}$C or T$_{11}$G), 20 µM of dNTPs, RNA and RT buffer [25 mM Tris-Cl (pH, 8.3), 37.6 mM KCl, 1.5 MM MgCl$_2$ and 5mM DTT]. In the present invention, dNTP refers to deoxy nucleoside triphosphate, which comprises of deoxyadenosine triphosphate (hereinafter referred to dATP), deoxyguanosine triphosphate (hereinafter referred to dGTP), deoxycytidine triphosphate (hereinafter referred to dCTP) and deoxythymidine triphosphate (hereinafter referred to dTTP). Three RT reactions were set per RNA sample for the corresponding T$_{11}$M primer. The reactions were carried out in a thermocycler (model 480 from M/s Perkin-Elmer, USA). Thermocycler parameters chosen for reverse transcription were 65° C. for 5 minutes, →37° C. for 60 minutes, →75° C. for 5 minutes, →4° C. (till the samples are removed). 100 units of reverse transcriptase was added to each reaction after 10 minute incubation at 37° C. and reaction then continued for rest of the 50 minutes. Four different RNA in combination with 3 T$_{11}$M primers yielded a total of 12 reactions depicting 12 different classes of cDNAs. The use of 3 different T$_{11}$M primers divided the whole RNA population into 3 sub-classes depending upon the anchored base M, which was either A, C or G (Reverse transcription system was a component of RNAimage kit from M/s. GenHunter Corporation, USA).

Example 4

Generation of a Spectrum of Differentially Expressed Genes Through Differential Display of mRNA for Identification of Differentially Expressed Gene(s):

Different sub-classes of cDNA from CO, DS, RC and AB RT product as obtained in Example 2 were amplified in the presence of a radiolabelled dATP to label the amplified product through polymerase chain reaction (hereinafter known as PCR; PCR process is covered by patents owned by Hoffman-La Roche Inc.). Radioactive PCR was carried out in 20 µl reaction mix containing a (1) reaction buffer [10 mM Tris-Cl (pH, 8.4), 50 mM KCl, 1.5 mM MgCl$_2$, 0.001% gelatin], (2) 2 µM dNTPs, (3) 0.2 µM T$_{11}$M and (4) 0.2 µM arbitrary primers (chemicals 1 to 4 were purchased from M/s. GenHunter Corporation, Nashville, USA as a part of RNAimage kit), 0.2 µl α[$^{33}$P] dATP (~2000 Ci/mmole, purchased from JONAKI Center, CCMB campus Hyderabad, India), and 1.0 units of *Thermus aqueticus* (hereinafter referred to Taq) DNA Polymerase (purchased from M/S. Qiagen, Germany). 30 µl of autoclaved mineral oil was overlaid at the top of each reaction to avoid alteration in volume due to evaporation. T$_{11}$M primer in each reaction was the same that was used to synthesize cDNA. Parameters chosen were: 40 cycles of 94° C. for 30 seconds, →40° C. for 2 minutes, →72° C. for 30 seconds; and 1 cycle of 72° C. for 5 minutes and final incubation at 4° C.

Figure 3:
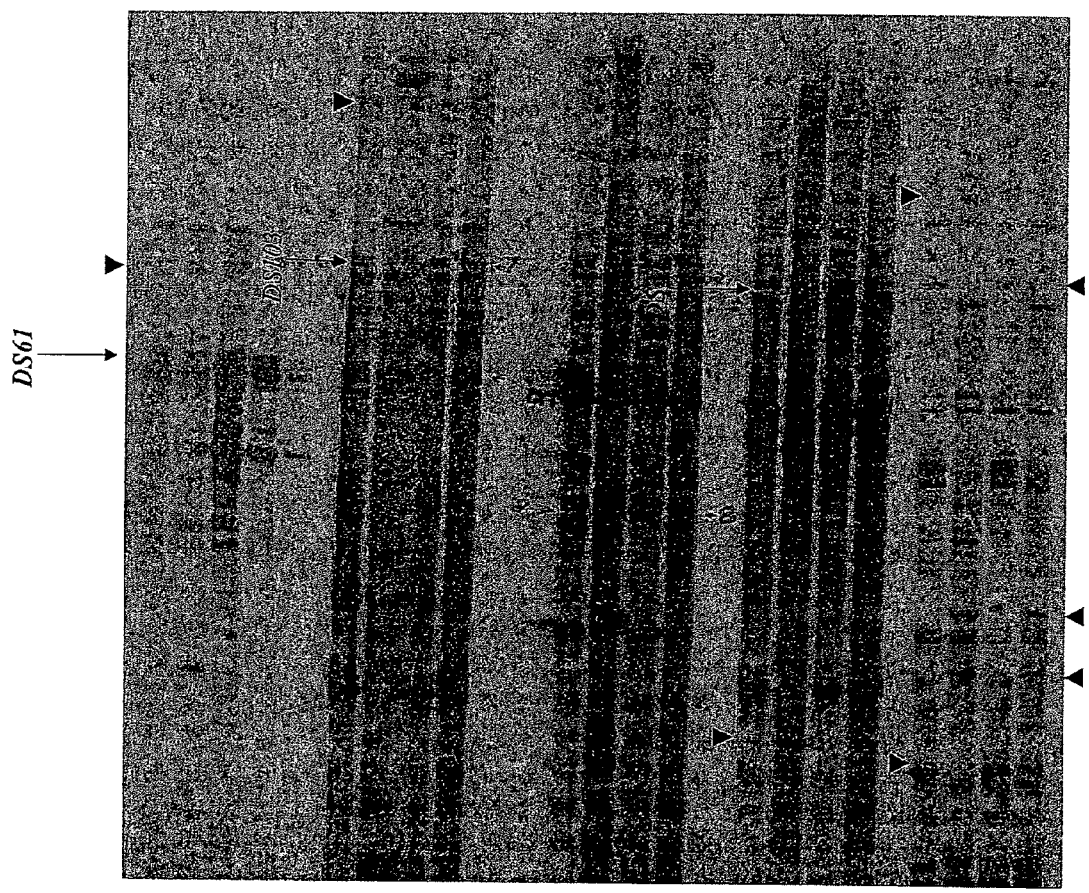
FIG. 3 represents spectrum of 3' ends of the expressed and repressed genes in $4^{th}$ leaf in response to CO, DS, RC and AB using the primer combinations as defined at the bottom of each lane. Arrow indicates differential expression.
Figure 4:
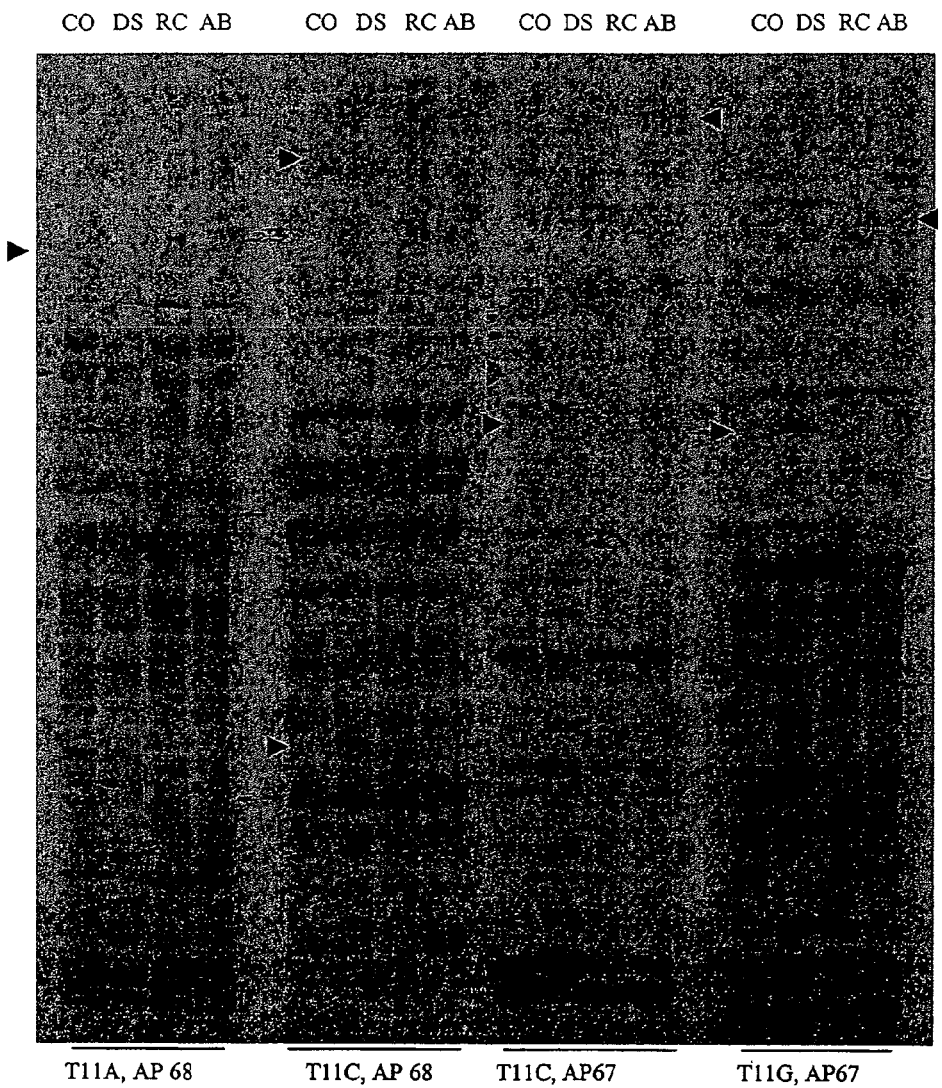
FIG. 4 represents spectrum of 3' ends of the expressed and repressed genes in $4^{th}$ leaf in response to CO, DS, RC and AB using the primer combinations as defined at the bottom of each lane. Arrow indicates differential expression.

Amplified products were fractionated onto a 6% denaturating polyacrylamide gel. For the purpose 3.5 µl of each of amplified product was mixed with 2 µl of loading dye [95% formamide, 10 mM EDTA (pH, 8.0), 0.09% xylene cyanol FF and 0.09% bromophenol blue], incubated at 80° C. for 2 minutes and loaded onto a 6% denaturating polyacrlamide gel [denaturating polyacrylamide gel: 15 ml of acrylamide (40% stock of acrylamide and bisacrylamide in the ratio of 20:1), 10 ml of 10×TBE, 40 ml of distilled water and 50 g urea]. Electrophoresis was performed using 1×TBE buffer [10× TBE: 108 g Tris base, 55 g boric acid and 40 ml of 0.5 M EDTA (pH, 8.0)] as a running buffer at 60 watts until the xylene cyanol (the slower moving dye) reached the lower end of the glass plates. Size of the larger plate of the sequencing gel apparatus was 13×16 inch. After the electrophoresis, one of the glass plates was removed and the gel transferred onto a 3 MM Whattman filter paper. Gel was dried at 80° C. under vacuum overnight and exposed to Kodak X-ray film for 2-3 days. Before exposing to X-ray film, corners of the dried gel were marked with radioactive ink for further alignment. FIGS. 3-4 show the spectrum of differentially expressed genes in CO, DS, RC and AB 4th leaf of tea as was seen after developing the film. After developing the gel, film was analyzed for differentially expressed bands between CO, DS, RC and AB signals.

Sequences of the primers used for differential display were as follows (purchased from M/s. GenHunter Corporation, USA as a part of RNAimage kit):

| T11M (anchored) primers | Primer sequence | |
|---|---|---|
| T11A | 5'-AAGCTTTTTTTTTTTTA-3' | SEQ ID NO:16 |
| T11C | 5'-AAGCTTTTTTTTTTTTC-3' | SEQ ID NO:17 |
| T11G | 5'-AAGCTTTTTTTTTTTTG-3' | SEQ ID NO:18 |

| Arbitrary Primers | Primer Sequence | |
|---|---|---|
| AP1 | 5'-AAGCTTGATTGCC-3' | SEQ ID NO:19 |
| AP36 | 5'-AAGCTTCGACGCT-3' | SEQ ID NO:20 |
| AP37 | 5'-AAGCTTGGGCCTA-3' | SEQ ID NO:21 |
| AP65 | 5'-AAGCTTCAAGACC-3' | SEQ ID NO:22 |
| AP66 | 5'-AAGCTTGCCTTTA-3' | SEQ ID NO:23 |
| AP67 | 5'-AAGCTTTATTTAT-3' | SEQ ID NO:24 |
| AP68 | 5'-AAGCTTCTTTGGT-3' | SEQ ID NO:25 |

Example 5

Reamplification of cDNA Probes:

Cloning the differentially expressed bands required elution of the same from the denaturating polyacrylamide gel and further amplification to yield substantial quantity of DNA for the purpose of cloning. Autoradiogram (developed X-ray film) was oriented with the dried gel aided with radioactive ink. The identified differentially expressed band (along with the gel and the filter paper) was cut with the help of a sterile sharp razor. DNA was eluted from the gel and the filter paper by incubating them in 100 μl of sterile $dH_2O$ for 10 min in an eppendorf tube, followed by boiling for 10 minutes. Paper and gel debris were pelleted by spinning at 10,000 rpm for 2 min and the supernatant containing DNA was transferred into a new tube. DNA was precipitated with 10 μl of 3M sodium acetate, pH, 5.5, 5 μl of glycogen (concentration of stock: 10 mg/ml) and 450 μl of ethanol. After an overnight incubation at −70° C., centrifugation was performed at 10,000 rpm for 10 min at 4° C. and pelleted DNA was rinsed with 85% ethanol. DNA pellet was dissolved in 10 μl of sterile distilled water.

Figure 5:
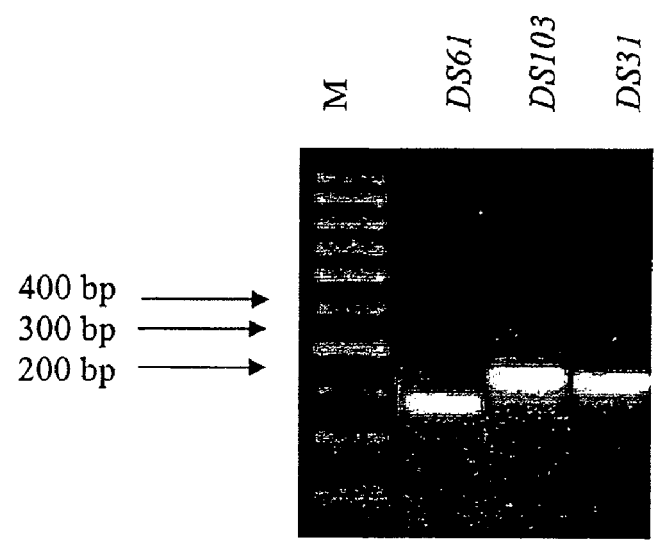
FIG. 5 represents amplification of the differentially expressed 3' ends of the gene after eluting from the denaturating polyacrylamide gel. M represents DNA size marker.

Eluted DNA was amplified using the same set of $T_{11}M$ and arbitrary primer that was used for the purpose of performing differential display as in the Example 4. Also, the PCR conditions were the same except that dNTP concentration was 20 μM instead of 2 μM and no isotopes were added. Reaction was up-scaled to 40 μl and after completion of PCR, 30 μl of PCR sample was run on 1.5% agarose gel in TAE buffer (TAE buffer: 0.04 M Tris-acetate, 0.002 M EDTA, pH 8.5) containing ethidium bromide (final concentration of 0.5 μg/ml) (see FIG. 5). Rest of the amplified product was stored at −20° C. for cloning purposes.

Example 6

Cloning of Re-amplified PCR Products:

Re-amplified PCR products as obtained in example 4 were ligated in 300 ng of insert-ready vector called as PCR-TRAP® vector using 200 units of $T_4$ DNA-ligase in 1×ligation buffer (10× ligase buffer: 500 mM Tris-Cl, pH 7.8, 100 mM $MgCl_2$, 100 mM DTT, 10 mM ATP, 500 μg/ml BSA). Vector and the other chemicals required were purchased from M/s. GenHunter Corporation, Nashville, USA as PCR-TRAP® cloning system. Ligation was performed at 16° C. for 16 hours in a thermocycler model 480 from M/s. Perkin Elmer, USA. Ligation of the PCR product into a vector such as above yields to a circularized plasmid. The process of ligation of the foreign DNA, such as the PCR product in the present invention, into a suitable vector, such as PCR-TRAP® vector in the present invention, is known as cloning. There is a range of other vectors that are commercially available or otherwise that suit the cloning work of PCR products and hence, may be used. The plasmid, as per the definition, is a closed cicular DNA molecule that exists in a suitable host cell such as in *Escsherichia coli* (hereinafter referred to *E. coli*) independent of chromosomal DNA and may confer resistance against an antibiotic. PCR-TRAP® vector resulting plasmid confers resistance against tetracycline.

Ligated product or the plasmid needs to be placed in a suitable *E. coli* host for its multiplication and propagation through a process called transformation. Ligated product (10 μl) as obtained above was used to transform 100 μl of competent *E. coli* cells (purchased from M/s. GenHunter Corporation USA as a part of PCR-TRAP® cloning system). Competent means the *E. coli* cells capable of accepting a plasmid DNA. For this purpose, ligated product and competent cell were mixed, kept on ice for 45 minutes, heat shocked for 2 minutes and cultured in 0.4 ml of LB medium (LB medium: 10 g tryptone, 5 g yeast extract, 10 g sodium chloride in 1 liter of final volume in distilled/deionized water) for 4 hours. 200 μl of transformed cells were plated onto LB-tetracyclin (for 1 liter: 10 g tryptone, 5 g yeast extract, 10 g sodium chloride, and tetracyclin added to a final concentration of 20 μg/ml) plates and grown overnight at 37° C. Colonies were marked and single isolated colony was restreaked on to LB-tetracyclin plates to get colonies of the same kind. Conferral of tetracyclin resistance to *E. coli* cells apparently suggests that the PCR product i.e. the identified gene has been cloned.

In whole of the above process, the selection of $T_{11}M$ primer will amplify the poly A tail region of mRNA. Poly A tail is always attached to 3' end of the gene and hence $T_{11}M$ primer in combination with an arbitrary primer would always yield 3' region of the gene.

Example 7

Checking the Size of the PCR Product

Once the gene has been cloned and the *E. coli* transformed, it becomes imperative to check if the plasmid has received right size of the PCR product. This can be accomplished by performing colony PCR wherein the colony is lysed and the lysate containing template, is subsequently used to perform PCR using the appropriate primers. Amplified product is then analysed on an agarose gel.

Figure 6:
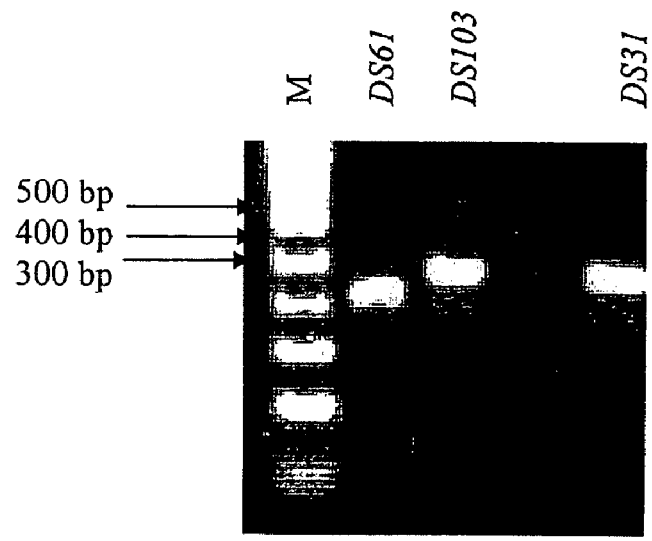
FIG. 6 represents amplification after cloning of the eluted differentially expressed 3' ends of the gene as mentioned in FIG. 5. M represents DNA size marker.

Colonies were picked up from re-streaked plates (Example 6) and lysed in 50 μl colony lysis buffer [colony lysis buffer: TE (Tris-Cl 10 mM, 1 mM EDTA, pH 8.0) with 0.1% tween 20] by boiling for 10 minutes. Cell debris were pelleted and the supernatant or the colony lysate containing the template DNA was used for PCR. PCR components were essentially the same as in example 4 except that in place of $T_{11}M$ and arbitrary primers, Lgh (5'-CGACAACACCGATAATC-3'; SEQ ID NO: 14) and Rgh (5'-GACGCGAACGAAGCAAC-3'; SEQ ID NO: 15) primers (specific to the vector sequences flanking the cloning site) were used and 2 μl of the colony lysate was used in place of eluted DNA. Also, the reaction volume was reduced to 20 μl. PCR conditions used for colony PCR were, 94° C. for 30 seconds, →52° C. for 40 seconds, →72° C. for 1 minute for 30 cycles followed by 1 cycle of 5 min extension at 72° C. and final soaking into 4° C. Amplified product were run on 1.5% agarose gel along with molecular weight marker and analyzed for correct size of insert. While using Lgh and Rgh flanking primers, the size of the cloned PCR product was larger by 120 bp due to the flanking vector sequence being amplified (See FIG. 6).

Example 8

Confirmation of the Differential Expression by Northern Blotting

PCR products cloned above represent 3' end of the differentially expressed genes. Within the scope of the present invention, these cloned fragments of DNA will be called as genes. Since differential display invariably leads to false positives i.e. apparently differentially expressed genes (Wan, J. S. and Erlander, M. G. 1997. Cloning differentially expressed genes by using differential display and subtractive hybridization. In Methods in Molecular Biology. Vol. 85: Differential display methods and protocols. Eds. Liang, P. and Pardee, A. B. Humana press Inc., Totowa, N.J., pp. 45-68), a confirmatory test through northern analysis is mandatory to ascertain differential expression between CO, DS, RC and AB 4th leaf of tea. Northern analysis requires preparation of a radio-labelled probe followed by its hybridization with denatured RNA blotted onto a membrane.

Amplified products as in Example 7 were used as a probe in northern analysis. After visualising the amplified products on 1.5% agarose gel, these were cut from the gel and the DNA was eluted from the gel using QIAEX II gel extraction kit from M/s. Qiagen, Germany following the manufacturer's instructions.

Purified fragments were radiolabelleled with $\alpha[^{32}P]dATP$ (4000 Ci/mmole) using HotPrime Kit from M/s. GenHunter Corporation, Nashville, USA following their instructions. Radio-labelled probe was purified using QIAquick nucleotide Removal Kit (QIAGEN, Germany) to remove unincorporated radionucleotide.

For blotting, 20 μg of RNA was run on 1.0% formaldehyde agarose gel essentially as described in Example 2. Once the run was completed, gel was washed twice with DEPC treated autoclaved water for 20 minutes each with shaking. Gel was then washed twice with 10×SSPE (10×SSPE: 1.5 M sodium chloride, 115 mM $NaH_2PO_4$, 10 mM EDTA) for 20 minutes each with shaking. In the mean time nylone membrane (Boehringer mannheim cat. no.# 1209272) was wetted in DEPC water and then soaked in 10×SSPE for 5 minutes with gentle shaking. RNA from the gel was then vacuum-blotted (using pressure of 40 mbar) onto nylon membrane using DEPC-treated 10×SSPE as a transfer medium. Transfer was carried out for 4 hours. Pressure was Increased to 70 mbar for 15 minutes before letting out the gel from the vacuum blotter. After the transfer, gel was removed, and the location of RNA marker was marked on the nylon surface under a UV light source. Membrane was dried and baked at 80° C. for 45 minutes. After a brief rinse in 5×SSPE (20×SSPE: 3M sodium chloride, 230 mM sodium phosphate, 20 mM EDTA) membrane was dipped into prehybridization solution (50% formamide, 0.75 M NaCl, 50 mM sodium phosphate, pH 7.4, 5 mM EDTA, 0.1% Ficoll-400, 0.1% BSA, 0.1% polyvinypyrollidone, 0.1% SDS solution and 150 ug/ml freshly boiled salmon sperm DNA) for 5 hours.

Radiolabelled probe synthesized earlier was denatured, by boiling for 10 minutes followed by addition to the prehybridization solution dipping the blotted membrane. Hybridization was carried out for 16 hours. Solution was removed and the membrane was washed twice with 1×SSC (20×SSC; 3M sodium chloride and 0.3M sodium citrate dihydrate, pH, 7.0) containing 0.1% SDS at room temperature for 15 minutes each. Final washing was done at 50° C. using pre-warmed 0.25×SSC containing 0.1% SDS for 15 minutes. Membrane was removed, wrapped in saran wrap and exposed to X-ray film for 12-240 hours depending upon the intensity of the signal.

Figure 7:
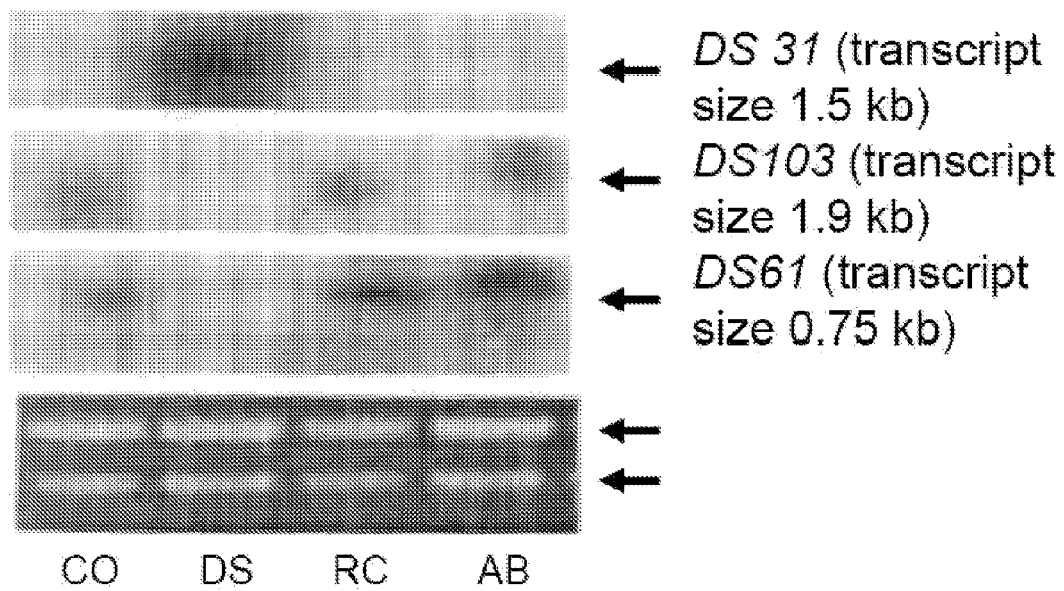
FIG. 7 represents confirmation of differential expression through northern hybridization of the cloned 3' ends of the gene.

While performing northern hybridization, RNA from CO, DS, RC and AB 4th leaf are blotted on the membrane and tested for the probe of choice. FIG. 7 shows the results with 3 such probes and confirm differential expression between CO, DS, RC and AB 4th leaf. Three genes that showed confirmed differential expression and are designated as

DS 31 (T11G, AP65)
DS 61 (T11A, AP1)
DS103 (T11A, AP65)

Various primer combinations used to clone the genes are depicted inside the bracket. The details of these primers are mentioned in example 4.

DS 31 (T11G, AP65), which is basically a 3' end region of the gene, hybridized to the transcript of 1.5 kilobase size on northern blot as in FIG. 7.

DS 61 (T11A, AP1), which is basically a 3' end region of the gene, hybridized to the transcript of 750 base size on northern blot as in FIG. 7.

DS103 (T11A, AP 65), which is basically a 3' end region of the gene, hybridized to the transcript of 1.9 kilobase size on northern blot as in FIG. 7.

Size of the above transcript has been measured with the help of RNA markers (Cat# R7020) purchased from M/S. Sigma chemical company, USA Example 9

All the sequences were searched for uniqueness in the gene databases available at URL www.ncbi.nlm.nih.gov. using BLAST (BLAST stands for Basic Local Alignment Search Tool). It may be appreciated from the results that for the sequence ID 1, out of 318 bases maximum bit value was 107 and also the maximum identity was 107 bases (33.6%). Such a low identity in sequence with the known sequences confers novelty to the cloned sequence. Analysis further revealed (Annexure 1) that dr31 showed very significant score (ranging between 8e-22 to 3e-9) with 3' end of the genes for (1) thaumatin like proteins (TLP) from *Vitis vinifera, Glycine max* and *Nicotiana tabacum*; (2) pathogenesis-related (PR) protein R major form with *N. tabacum* mRNA (E value, 1e-17); and (3) partial o1p2 gene for osmotin-like protein (OLP) from *Fagus sylvatica* (E value, 8e-19) (E value or the Expectation value as defined under the glossary of BLAST programme is as follows:

The number of different alignments with scores equivalent to or better than S that are expected to occur in a database search by chance. The lower the E value, the more significant the score). TLP, PR protein with R major form and OLP, all the three belong to PR-5 family of PR proteins, which are known to be induced in response to fungal attack and during osmotic stress (Singh N. K., Bracker C. A., Hasegawa P. M., Handa A. K., Buckel S., Hermodon M. A., Pfankoch E., Regnier F. E., Bressan R. A. 1987. Charaterization of osmotin. A thaumatin-like protein associated with osmotic adaptation to plant cells. *Plant Physiology* 85, 529-536; Yun D. J., Bressan R. A., Hasegawa P. M. 1997. Plant antifungal proteins. *Plant Breeding Reviews*. 14: 39-88). PR-5 family proteins and hence these genes are implicated in conferring protection against fungal attack and drought. Thus, one of the mechanisms by which tea is protected against deleterious effects of drought is through the over production of PR-5 like genes.

It may be appreciated from the results for the sequence ID 2, out of 251 bases, maximum bit score was 52 and maximum identity was 26 bases (10.4%). Such a low identity in sequence with the known sequences confers novelty to the cloned sequence. Sequence homology search showed significant score (3e-4) of ID2 sequence with 3' ends of chicken calsequestrin mRNA. Calsequestlin is a calcium binding protein that is very well reported in animal system and found in the heart and skeletal muscle (Cala, S E, Jones, L R. 1983. Rapid purification of calsequestrin from cardiac and skeletal muscle sacroplasmic reticulum vesicles by $Ca^{2+}$-dependent elution from phenyl-sepharose.

*Journal of Biological Chemistry* 258, 11932-11936). The protein is involved in the regulation of intracellular $Ca^{++}$ homeostasis, apart from its role as a calcium storage protein. Immunological studies in red beet and cucumber cell showed that a 55 kDa polypeptide cross-reacted with a monoclonal antibody raised against calsequestrin from rabbit skeletal muscle.

These Calsequestrin like proteins were implicated in cellular Ca++ regulation.

Incidentally, drought/osmotic stress mediate enhancement of cytosolic Ca++, which are known to trigger drought-induced genes with protective function (Knight H, Brandt-S, Knight M R. 1998. A history of stress alters drought calcium signaling pathways in Arabidopsis. *The Plant Journal* 16, 681-687; Knight H, Trewavas A J, Knight M R. 1997. Calcium signaling in *Arabidopsis thaliana* responding to drought and salinity. *The Plant Journal* 125, 1067-1078). Suppression of calsequestrin would lead to enhancement of cytosolic Ca++ levels, thus triggering array of drought-induced genes. Data thus suggests that calsequestrin may be involved in signal transduction pathway under drought situations in tea.

It may be appreciated from the results for the sequence ID 3, out of 361 bases maximum bit score was 40 and maximum identity was 23 (11.1%). Such a low identity in sequence with the known sequences confers novelty to the cloned sequence, however E values care higher (in positive) and hence it is difficult to assign anyrole to the sequences till the complete gene is cloned and sequenced.

These sequences were designated to be novel in context to the present invention since their homology was found to be less than 35% with any of the sequences submitted in the databases available to the public till March, 2002.

The Main Advantages of the Present Invention are:
- Three hovel genes that facilitate water-stress tolerance in plants.
- Novel genes that facilitate drought tolerance more particularly in tea plants.
- A method to clone the novel genes related to drought stress.
- Spectra of 3' ends of the expressed and repressed genes in CO, DS, RC and AB leaves of tea for identification of differentially expressed genes have been presented.
- Confirmation of the identified 3' ends of the differentially expressed gene(s) for establishing differential expression in leaves of tea experiencing drought stress.
- Sequencing of the cloned 3' ends of the differentially expressed gene(s) showed uniqueness in terms of novel sequences not deposited in the data bank so far.
- A method of introducing drought tolerance in plant systems.
- A method of introducing drought tolerance in tea plants.

SEQUENCE LISTING

```
<160> NUMBER OF SEQ ID NOS: 28

<210> SEQ ID NO 1
<211> LENGTH: 318
<212> TYPE: DNA
<213> ORGANISM: Camellia sinensis

<400> SEQUENCE: 1
aatcaatatt gttgcactca tgggcctggg atcatgtggg cctggatcat gtgggcctac      60
acctttgtcc aagttcttca aggataggtg cccagatgct tatagctatc ctcaggatga     120
tccaaccagt ttgttcactt gtcctcctgc tggtaccaat tattgcctat accttctgcc     180
cttgaggcct cttttcact cccttccctc tctttataat tataggacag tgttatagta      240
caataagacc tcactagttt caatatttgt gagattcaga cactgtgttt aattaaattt     300
gtgacattta gtgttgtc                                                  318

<210> SEQ ID NO 2
<211> LENGTH: 251
<212> TYPE: DNA
<213> ORGANISM: Camellia sinensis

<400> SEQUENCE: 2
aataagaagg ggtcttgact agcccctgtt atatgagacg tgaggagcga tggcgatgac      60
gatgatgacg atgatgatgt tggtgtggca gccagccgca taactttttt cagtttttgat    120 tgtctaaggt tttgatatgt taatggtcag ctaagcaaat acatgagctc atatattcag     180
tacttggcat ataaataacc tgtcttgcta ttcatattaa tgttctagat atgataatca     240
ccttctctct c                                                         251

<210> SEQ ID NO 3
<211> LENGTH: 361
<212> TYPE: DNA
<213> ORGANISM: Camellia sinensis

<400> SEQUENCE: 3
```

```
atcggcaaca gatgttgaaa ctcaccttac actaatgtgt ccagatcttc tcaacaggaa      60
ttctagcaac cgaggacacc actatgatgt gtccagctct tctcaacagg aattgtagca     120
atttagacaa ccgaggacac cactatacat acatacaagc atggttttaa ataaagcgtt     180
cacatagctg atatcagata ctattgacgt gcagatattg ttgaatatcg gtatcaatat     240
tttaaaacca tgcatatgag agttcaacac aagttagaag ctctcttttg ttttcatttt     300
acaagtttgt gtaatttgat gtaagagcaa aagcttagta tatgtaatga gaattttgaa     360
c                                                                     361
```

<210> SEQ ID NO 4
<211> LENGTH: 5
<212> TYPE: DNA
<213> ORGANISM: Arabidopsis thaliana
<220> FEATURE:
<221> NAME/KEY: misc_feature
<223> OTHER INFORMATION: as1

<400> SEQUENCE: 4

```
tgacg                                                                   5
```

<210> SEQ ID NO 5
<211> LENGTH: 6
<212> TYPE: DNA
<213> ORGANISM: Arabidopsis thaliana
<220> FEATURE:
<221> NAME/KEY: misc_feature
<223> OTHER INFORMATION: sp1

<400> SEQUENCE: 5

```
gggcgg                                                                  6
```

<210> SEQ ID NO 6
<211> LENGTH: 7
<212> TYPE: DNA
<213> ORGANISM: Arabidopsis thaliana

<400> SEQUENCE: 6

```
tggttag                                                                 7
```

<210> SEQ ID NO 7
<211> LENGTH: 6
<212> TYPE: DNA
<213> ORGANISM: Arabidopsis thaliana

<400> SEQUENCE: 7

```
cacatg                                                                  6
```

<210> SEQ ID NO 8
<211> LENGTH: 9
<212> TYPE: DNA
<213> ORGANISM: Arabidopsis thaliana

<400> SEQUENCE: 8

```
taccgacat                                                               9
```

<210> SEQ ID NO 9
<211> LENGTH: 8
<212> TYPE: DNA
<213> ORGANISM: Arabidopsis thaliana
<220> FEATURE:
<221> NAME/KEY: misc_feature
<222> LOCATION: (1)..(1)
<223> OTHER INFORMATION: y= pyrimidine: t or c

```
<400> SEQUENCE: 9 yacgtggc                                                                  8

<210> SEQ ID NO 10
<211> LENGTH: 6
<212> TYPE: DNA
<213> ORGANISM: Arabidopsis thaliana

<400> SEQUENCE: 10 cacgtg                                                                    6

<210> SEQ ID NO 11
<211> LENGTH: 9
<212> TYPE: DNA
<213> ORGANISM: Arabidopsis thaliana

<400> SEQUENCE: 11 taccgacat                                                                 9

<210> SEQ ID NO 12
<211> LENGTH: 6
<212> TYPE: DNA
<213> ORGANISM: Arabidopsis thaliana
<220> FEATURE:
<221> NAME/KEY: misc_feature
<222> LOCATION: (1)..(6)
<223> OTHER INFORMATION: y= pyrimidine: t or c; r= purine: g or a

<400> SEQUENCE: 12 yaacyr                                                                    6

<210> SEQ ID NO 13
<211> LENGTH: 6
<212> TYPE: DNA
<213> ORGANISM: Arabidopsis thaliana
<220> FEATURE:
<221> NAME/KEY: misc_feature
<222> LOCATION: (3)..(4)
<223> OTHER INFORMATION: n= a or t or g or c or other or unknown

<400> SEQUENCE: 13 canntg                                                                    6

<210> SEQ ID NO 14
<211> LENGTH: 17
<212> TYPE: DNA
<213> ORGANISM: Camellia sinensis

<400> SEQUENCE: 14
cgacaacacc gataatc                                                       17

<210> SEQ ID NO 15
<211> LENGTH: 17
<212> TYPE: DNA
<213> ORGANISM: Camellia sinensis

<400> SEQUENCE: 15
gacgcgaacg aagcaac                                                       17

<210> SEQ ID NO 16
<211> LENGTH: 18
<212> TYPE: DNA
<213> ORGANISM: Camellia sinensis
```

-continued

```
<400> SEQUENCE: 16 aagcttttttt tttttttta                                                18

<210> SEQ ID NO 17
<211> LENGTH: 18
<212> TYPE: DNA
<213> ORGANISM: Camellia sinensis

<400> SEQUENCE: 17 aagcttttttt tttttttc                                                 18

<210> SEQ ID NO 18
<211> LENGTH: 18
<212> TYPE: DNA
<213> ORGANISM: Camellia sinensis

<400> SEQUENCE: 18 aagcttttttt tttttttg                                                 18

<210> SEQ ID NO 19
<211> LENGTH: 13
<212> TYPE: DNA
<213> ORGANISM: Camellia sinensis

<400> SEQUENCE: 19
aagcttgatt gcc                                                       13

<210> SEQ ID NO 20
<211> LENGTH: 13
<212> TYPE: DNA
<213> ORGANISM: Camellia sinensis

<400> SEQUENCE: 20
aagcttcgac gct                                                       13

<210> SEQ ID NO 21
<211> LENGTH: 13
<212> TYPE: DNA
<213> ORGANISM: Camellia sinensis

<400> SEQUENCE: 21
aagcttgggc cta                                                       13

<210> SEQ ID NO 22
<211> LENGTH: 13
<212> TYPE: DNA
<213> ORGANISM: Camellia sinensis

<400> SEQUENCE: 22
aagcttcaag acc                                                       13

<210> SEQ ID NO 23
<211> LENGTH: 13
<212> TYPE: DNA
<213> ORGANISM: Camellia sinensis

<400> SEQUENCE: 23
aagcttgcct tta                                                       13

<210> SEQ ID NO 24
<211> LENGTH: 13
<212> TYPE: DNA
<213> ORGANISM: Camellia sinensis
```

<400> SEQUENCE: 24
aagctttatt tat                                                            13

<210> SEQ ID NO 25
<211> LENGTH: 13
<212> TYPE: DNA
<213> ORGANISM: Camellia sinensis

<400> SEQUENCE: 25
aagcttcttt ggt                                                            13

<210> SEQ ID NO 26
<211> LENGTH: 347
<212> TYPE: DNA
<213> ORGANISM: Camellia sinensis
<220> FEATURE:
<221> NAME/KEY: misc_feature
<222> LOCATION: (1)..(13)
<223> OTHER INFORMATION: AP65 Arbitrary Primer
<220> FEATURE:
<221> NAME/KEY: misc_feature
<222> LOCATION: (319)..(347)
<223> OTHER INFORMATION: T11G Anchor Primer

<400> SEQUENCE: 26
aagcttcaag accaatcaat attgttgcac tcatgggcct gggatcatgt gggcctggat          60
catgtgggcc tacacctttg tccaagttct tcaaggatag gtgcccagat gcttatagct         120
atcctcagga tgatccaacc agtttgttca cttgtcctcc tgctggtacc aattattgcc         180
tataccttct gcccttgagg cctcttttc actcccttcc ctctctttat aattatagga          240
cagtgttata gtacaataag acctcactag tttcaatatt tgtgagattc agacactgtg         300
tttaattaaa tttgtgacat ttagtgttgt ccaaaaaaaa aaagctt                       347

<210> SEQ ID NO 27
<211> LENGTH: 276
<212> TYPE: DNA
<213> ORGANISM: Camellia sinensis
<220> FEATURE:
<221> NAME/KEY: misc_feature
<222> LOCATION: (1)..(13)
<223> OTHER INFORMATION: AP1 Arbitrary Primer
<220> FEATURE:
<221> NAME/KEY: misc_feature
<222> LOCATION: (252)..(276)
<223> OTHER INFORMATION: T11A Anchor Primer

<400> SEQUENCE: 27
aagcttgatt gccaataaga aggggtcttg actagcccct gttatatgag acgtgaggag          60
cgatggcgat gacgatgatg acgatgatga tgttggtgtg gcagccagcc gcataacmmc         120
agttttgatt gtctaaggtt ttgatatgtt aatggtcagc taagcaaata catgagctca         180
tatattcagt acttggcata taaataacct gtcttgctat tcatattaat gttctagata         240
tgataatcac cttctctctc taaaaaaaaa aagctt                                   276

<210> SEQ ID NO 28
<211> LENGTH: 390
<212> TYPE: DNA
<213> ORGANISM: Camellia sinensis
<220> FEATURE:
<221> NAME/KEY: misc_feature
<222> LOCATION: (1)..(13)
<223> OTHER INFORMATION: AP65 Arbitrary Primer
<220> FEATURE:

```
<221> NAME/KEY: misc_feature
<222> LOCATION: (362)..(389)
<223> OTHER INFORMATION: T11A Anchor Primer

<400> SEQUENCE: 28
aagcttcaag accatcggca acagatgttg aaactcacct tacactaatg tgtccagatc      60
ttctcaacag gaattctagc aaccgaggac accactatga tgtgtccagc tcttctcaac     120
aggaattgta gcaatttaga caaccgagga caccactata catacataca agcatggttt     180
taaataaagc gttcacatag ctgatatcag atactattga cgtgcagata ttgttgaata     240
tcggtatcaa tattttaaaa ccatgcatat gagagttcaa cacaagttag aagctctctt     300
ttgttttcat tttacaagtt tgtgtaattt gatgtaagag caaaagctta gtatatgtaa     360 tgagaattt gaactaaaaa aaaaaagctt                                        390
```

The invention claimed is:

1. An isolated polynucleotide comprising SEQ ID No. 1.

2. The isolated polynucleotide according to claim 1, wherein said polynucleotide is SEQ ID No. 1.

3. The isolated polynucleotide according to claim 1, wherein said polynucleotide is circular in shape.

4. The isolated polynucleotide according to claim 2, wherein said polynucleotide is circular in shape.

* * * * *